(12) United States Patent
Ghidini et al.

(10) Patent No.: US 8,710,037 B2
(45) Date of Patent: *Apr. 29, 2014

(54) PYRROLIDINE DERIVATIVES, PHARMACEUTICAL COMPOSITIONS CONTAINING THE SAME, AND METHODS OF USING THE SAME

(75) Inventors: Eleonora Ghidini, Parma (IT); Anna Maria Capelli, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/561,134

(22) Filed: Jul. 30, 2012

(65) Prior Publication Data

US 2013/0035320 A1 Feb. 7, 2013

(30) Foreign Application Priority Data

Aug. 1, 2011 (EP) .................................... 11176147

(51) Int. Cl.
 *C07J 71/00* (2006.01)
 *A61K 31/58* (2006.01)

(52) U.S. Cl.
 CPC ............. *C07J 71/0052* (2013.01); *A61K 31/58* (2013.01)
 USPC .............................................. 514/176; 540/49

(58) Field of Classification Search
 CPC ....................................... C07J 71/0052
 USPC .............................................. 540/49; 514/176
 See application file for complete search history.

(56) References Cited

U.S. PATENT DOCUMENTS

| 2011/0065678 A1 | 3/2011 | Armani et al. |
| 2011/0201580 A1 | 8/2011 | Ghidini et al. |
| 2012/0234316 A1 | 9/2012 | Ghidini et al. |
| 2012/0238531 A1 | 9/2012 | Ghidini et al. |

OTHER PUBLICATIONS

U.S. Appl. No. 13/964,928, filed Aug. 12, 2013, Ghidini.

*Primary Examiner* — Barbara P Badio
(74) *Attorney, Agent, or Firm* — Oblon, Spivak, McClelland, Maier & Neustadt, L.L.P.

(57) ABSTRACT

Novel anti-inflammatory and antiallergic compounds of the glucocorticosteroid series according to formulae (I) and (I') are effective for the prevention and/or treatment of diseases in which the number, activity, and movement of inflammatory cells is implicated.

24 Claims, No Drawings

PYRROLIDINE DERIVATIVES, PHARMACEUTICAL COMPOSITIONS CONTAINING THE SAME, AND METHODS OF USING THE SAME

CROSS REFERENCES TO RELATED APPLICATIONS

This application claims priority to European Patent Application No. 11176147.4 filed on Aug. 1, 2011, which is incorporated herein by reference in its entirety.

BACKGROUND OF THE INVENTION

1. Field of the Invention

The present invention relates to novel anti-inflammatory and anti-allergic compounds of the glucocorticosteroid series, methods of preparing such a compound, and pharmaceutical compositions which contain such a compound. The present invention also relates to combinations of such a compound and another active agent and to therapeutic uses of such a compound. More particularly, the present invention relates to glucocorticosteroids that are derivatives of pyrrolidine.

2. Discussion of the Background

Corticosteroids are potent anti-inflammatory agents, able to decrease the number, activity, and movement of inflammatory cells. Corticosteroids are commonly used to treat a wide range of chronic and acute inflammatory conditions including asthma, chronic obstructive pulmonary disease (COPD), allergic rhinitis, rheumatoid arthritis, inflammatory bowel disease and autoimmune diseases.

Corticosteroids mediate their effects through the glucocorticoid receptor (GR). The binding of corticosteroids to GR induces its nuclear translocation which, in turn, affects a number of downstream pathways via DNA-binding-dependent (e.g. transactivation) and DNA-binding-independent (e.g. transrepression) mechanisms.

Corticosteroids for treating chronic inflammatory conditions in the lung such as asthma and COPD are currently administered through inhalation. One of the advantages of employing inhaled corticosteroids (ICS) is the possibility of delivering the drug directly at the site of action, limiting systemic side-effects, thus resulting in a more rapid clinical response and a higher therapeutic ratio.

Although ICS treatment can yield important benefits, especially in asthma, it is important to minimize ICS systemic exposure which leads to the occurrence and severity of unwanted side effects that may be associated with chronic administration. Moreover, the limited duration of action of ICS currently available in the clinical practice contributes to suboptimal management of the disease. While the inhaler technology is the key point to target the lung, the modulation of the substituents on the corticosteroids molecular scaffold is important for the optimization of pharmacokinetic and pharmacodynamic properties in order to decrease oral bioavailability, confine pharmacological activity only in the lung (prodrugs and soft drugs) and increase systemic clearance. Moreover, long lasting ICS activity in the lung is highly desirable as once daily administration of ICS would allow the reduction of the frequency of administration and, thus, substantially improve patient compliance and, as a result, disease management and control. In sum, there is a pressing medical need for developing ICS with improved pharmacokinetic and pharmacodynamic characteristics.

Fluticasone furoate is an example of an enhanced affinity glucocorticoid that has been developed as topical therapy for allergic rhinitis with a unique combination of pharmacodynamic and physicochemical properties which render this compound long acting in the lung and rapidly inactivated by hepatic metabolism to reduce systemic side effects (Salter M, Biggadike K, Clackers M, et al. Fluticasone furoate (FF): enhanced cellular and tissue protection with a new selective glucocorticoid agonist [abstract no P212] Ann Allergy Asthma Immunol. 2007; 98:A89, which is incorporated herein by reference in its entirety).

Glucocorticoid pyrrolidine derivatives have not been described, except for the co-pending patent application PCT/EP2011/051537, which is incorporated herein by reference in its entirety, in which some pyrrolidine derivatives were described.

Thus, there remains a need for glucocorticoids with improved properties.

SUMMARY OF THE INVENTION

Accordingly, it is one object of the present invention to provide novel glucocorticoids.

It is another object of the present invention to provide novel methods of preparing such a glucocorticoid.

It is another object of the present invention to provide novel pharmaceutical compositions which contain such a glucocorticoid.

It is another object of the present invention to provide novel combinations which contain such a glucocorticoid and at least one other active agent.

It is another object of the present invention to provide novel methods of treating and/or preventing certain diseases and/or conditions by administering such a glucocorticoid.

These and other objects, which will become apparent during the following detailed description, have been achieved by the inventors' discovery that compounds of general formula (I), and the corresponding compounds of general formula (I') wherein, the configuration of some stereogenic centers is fixed are effective as glucocorticoids.

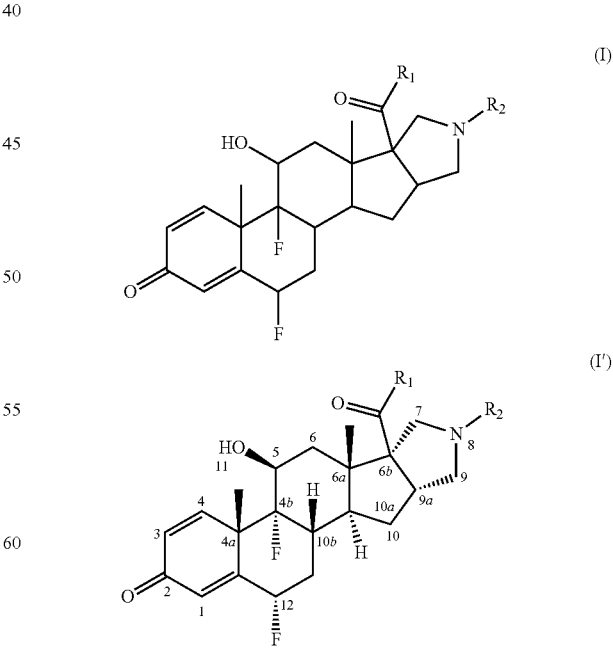

The present invention also provides pharmaceutically acceptable acid addition salts of compounds of formula (I)

and (I'), methods of preparing such a compound, combinations of such a compound with one or more active ingredients selected from the classes of β2-agonist, antimuscarinic agents, PDE4 inhibitors, P38 MAP kinase inhibitors and IKK2 inhibitors, pharmaceutical compositions containing such a compound, and therapeutic uses of such a compound or pharmaceutically acceptable salt.

Surprisingly, it has been found that the compounds of the invention show a particular good potency.

DETAILED DESCRIPTION OF THE PREFERRED EMBODIMENTS

According to a first aspect, the present invention is directed to compounds of general formula (I):

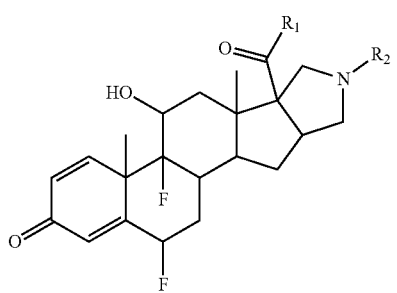

wherein
$R_1$ is $(CH_2)_n$—V—$(CH_2)_{n'}$—$R_4$, wherein
n and n' are independently 0 or 1;
V is absent or is selected from —O—, —S— and —OC(O)—;
$R_4$ is selected from the group consisting of:
—H, —OH, —CN or halogen;
$(C_1-C_6)$alkyl optionally substituted by one or more groups selected from oxo, —CN, —SH, or halogen;
$R_2$ is $(CH_2)_m$—$R_6$ wherein
m=0 or an integer from 1 to 4;
$R_6$ is selected from the group consisting of aryl and heteroaryl, optionally substituted by one or more groups selected from oxo, —OH, —CN, —COOH, $(C_1-C_6)$alkoxy, $(C_1-C_6)$alkyl, $(C_1-C_6)$haloalkyl, and halogen;
and pharmaceutically acceptable salts thereof.

The term "halogen atoms" includes fluorine, chlorine, bromine, and iodine.

The expression "$(C_1-C_6)$alkyl" refers to linear or branched alkyl groups wherein the number of constituent carbon atoms is in the range 1 to 6. Examples of alkyl groups are methyl, ethyl, n-propyl, isopropyl, t-butyl, n-pentyl, and n-hexyl.

The term "$(C_1-C_6)$alkoxy" refers to alkyl-oxy (e.g. alkoxy) groups, in which the alkyl portion is as above defined. Examples of said groups include methoxy, ethoxy, n-propoxy, isopropoxy, n-butoxy, isobutoxy, sec-butoxy, tert-butoxy, pentoxy, hexoxy, and the like.

The expression "$(C_1-C_6)$haloalkyl" refers to $(C_1-C_6)$alkyl wherein one or more hydrogen atoms are replaced by halogen atoms, which can be the same or different from each other. Examples of said $(C_1-C_6)$haloalkyl include halogenated, poly-halogenated, and fully halogenated alkyl groups wherein all of the hydrogen atoms are replaced by halogen atoms, e.g. trifluoromethyl group.

The expression "aryl" refers to mono, bi- or tricyclic ring systems which have 5 to 20 ring atoms, preferably from 5 to 15 ring atoms, and wherein at least one ring is aromatic.

Examples of suitable aryl monocyclic systems include benzene (phenyl) radicals and the like. Examples of suitable aryl bicyclic systems include naphthalene (naphthyl), biphenyl (biphenylene) radicals, and the like. Examples of suitable aryl tricyclic systems include fluorene (fluorenyl) radicals and the like.

The expression "heteroaryl" refers to mono-, bi-, or tricyclic ring systems which have 5 to 20 ring atoms, preferably from 5 to 15 ring atoms, in which at least one ring is aromatic and in which at least one ring atom is a heteroatom or a heteroatomic group selected from N, NH, S, and O.

Examples of suitable heteroaryl monocyclic systems include thiophene (thiophenyl), pyrrole (pyrrolyl), pyrazole (pyrazolyl), imidazole (imidazolyl), isoxazole (isoxazolyl), oxazole (oxazolyl), isothiazole (isothiaolyl), thiazole (thiazolyl), pyridine (pyridinyl), imidazolidine (imidazolidinyl), pyrimidine (pyrimidinyl), furan (furanyl) radicals, and the like.

Examples of suitable heteroaryl bicyclic systems include, purine (purinyl), pteridine (pteridinyl), benzotriazole benzotriazolyl), benzoimidazole (benzoimidazolyl), quinoline (quinolinyl), isoquinoline (isoquinolinyl), indole (indolyl), isoindole (isoindolyl), benzofuran (benzofuranyl), benzodioxane (benzodioxanyl), benzothiophene (benzothiophenyl), and the like.

Optionally, in any of the said rings including aryl, heteroaryl, one or more hydrogen atoms can be replaced by a group selected from halogen atoms, —OH, —CN, $(C_1-C_6)$alkyl, $(C_1-C_6)$haloalkyl, $(C_1-C_6)$alkoxy, and oxo.

The compounds of formula (I) contain asymmetric centers at the positions 4a, 4b, 5, 6a, 6b, 9a, 10a, 10b, and 12: the present invention is directed to all the possible stereoisomers and to mixtures thereof.

Preferably, the configuration of stereogenic centers is fixed: the configuration of the carbon atom in position 4a is S, 4b is R, 5 is S, in position 6a is S, in position 6b is S, in position 9a is R, in position 10a is S, in position 10b is S and in position 12 is S, as represented by the formula (I') below:

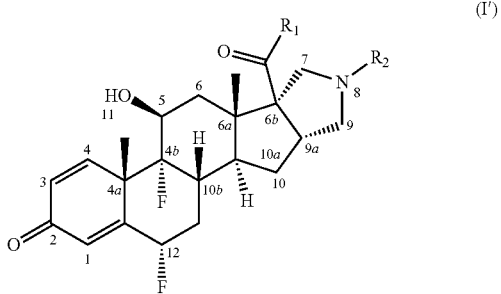

Compounds of general formula (I) and (I') may form acid addition salts with inorganic or organic acids or with bases such as amines or alkaline or alkali earth metal salts.

Suitable inorganic acids include hydrohalogen acids such as hydrofluoric acid, hydrochloric acid, hydrobromic acid, or hydroiodic acid, nitric acid, sulfuric acid, phosphoric acid; suitable organic acids include aliphatic monocarboxylic acids such as formic acid, acetic acid, trifluoroacetic acid, propionic acid; aliphatic hydroxy acids such as lactic, citric, tartaric or malic acids; dicarboxylic acids such as maleic or succinic acid; aromatic carboxylic acids such as benzoic acid; aromatic hydroxy acids and sulfonic acids.

A preferred group of compounds of general formula (I') is that wherein $R_1$ is $(CH_2)_n$—V—$(CH_2)_{n'}$—$R_4$, wherein n and n' are independently 0 or 1; V is absent or is selected from —O—, —S— and —OC(O)—; $R_4$ is selected from the group consisting of —H, —OH, —CN, halogen and $(C_1-C_6)$alkyl wherein one or more of the hydrogen atoms of the alkyl group may be optionally substituted by one or more groups selected from oxo, —CN, —SH or halogen.

Another preferred group of compounds of general formula (I') is that wherein $R_1$ is $(CH_2)_n$—V—$(CH_2)_{n'}$—$R_4$, wherein n is 0 or 1 and n' is 0; V is —O— and $R_4$ is —H.

Another preferred group of compounds of general formula (I') is that wherein $R_1$ is $(CH_2)_n$—V—$(CH_2)_{n'}$—$R_4$, wherein n is 0, V is —S— or —O—, n' is 1 and $R_4$ is fluorine or —CN.

Another preferred group of compounds of general formula (I') is that wherein $R_1$ is $(CH_2)_n$—V—$(CH_2)_{n'}$—$R_4$, wherein n is 1, V is absent, n' is 0 and $R_4$ is fluorine.

Another preferred group of compounds of general formula (I') is that wherein $R_1$ is $(CH_2)_n$—V—$(CH_2)_{n'}$—$R_4$, wherein n is 1, V is —OC(O)—, n' is 1 and $R_4$ is —H.

An even more preferred group of compounds of general formula (I') is that wherein $R_2$ is $(CH_2)_m$—$R_6$, wherein m=0 or 1 to 4; $R_6$ is selected from the group consisting of aryl and heteroaryl, optionally substituted by one or more groups selected from oxo, —OH, —CN, —C(O)OH, $(C_1-C_6)$alkoxy, $(C_1-C_6)$alkyl, $(C_1-C_6)$haloalkyl, and halogen.

Still more preferred are the compounds of general formula (I') wherein $R_2$ is $(CH_2)_m$—$R_6$, wherein m=0, $R_6$ is selected from phenyl, benzoimidazolyl, and quinolinyl, optionally substituted by one or more chlorine atoms.

An even more preferred group of compounds of general formula (I') is that wherein $R_2$ is $(CH_2)_m$—$R_6$, wherein m=1, $R_6$ is selected from phenyl, quinolinyl, and benzothiophenyl, optionally substituted by one or more chlorine atoms or methyl groups.

An even more preferred group of compounds of general formula (I') is that wherein $R_2$ is $(CH_2)_m$—$R_6$, wherein m=3 and $R_6$ is phenyl.

Whenever possible, it is to be understood that all of the preferred groups of compounds may be combined among each other.

The present invention also provides pharmaceutical compositions comprising a compound of formula (I) or (I') and one or more carriers and/or excipients.

The present invention also provides combinations of a compound of formula (I) or (I') with one or more active ingredients selected from β2-agonists, antimuscarinic agents, PDE4 inhibitors, P38 MAP kinase inhibitors, and IKK2 inhibitors.

The present invention also provides combinations of a compound of formula (I) or (I') with a β2-agonist selected from the group of carmoterol, GSK-642444, indacaterol, milveterol, arformoterol, formoterol, salbutamol, levalbuterol, terbutaline, AZD-3199, BI-1744-CL, LAS-100977, bambuterol, isoproterenol, procaterol, clenbuterol, reproterol, fenoterol, and ASF-1020.

The present invention also provides combinations of a compound of formula (I) or (I') with an antimuscarinic agent selected from aclidinium, tiotropium, ipratropium, trospium, glycopyrronium, and oxitropium.

The present invention also provides combinations of a compound of formula (I) or (I') with a PDE4 inhibitor selected from cilomilast, roflumilast, BAY19-8004, and SCH-351591.

The present invention also provides combinations of a compound of formula (I) or (I') with a P38 inhibitor selected from semapimod, talmapimod, pirfenidone, PH-797804, GSK-725, minokine, and losmapimod.

In a preferred embodiment, the present invention provides combinations of a compound of formula (I) or (I') with a IKK2 inhibitor.

The present invention also provides compounds of formula (I) or (I') for use as a medicament as well as the use of compounds of formula (I) or (I'), alone or combined with one or more active ingredients, for the preparation of a medicament for the prevention or treatment of any disease wherein the decrease in the number, activity, and movement of inflammatory cells is implicated, particularly of a disease of the respiratory tract characterized by airway obstruction such as asthma and COPD.

The invention provides a method for prevention and/or treatment of any disease wherein the decrease in the number, activity, and movement of inflammatory cells is implicated, said method comprising administering to a patient in need of such treatment a therapeutically effective amount of a compound of general formula (I) or (I'), alone or combined with one or more active ingredients. Examples of said diseases, include diseases of the respiratory tract characterized by airway obstruction such as asthma and COPD.

The pharmaceutical preparations of the invention are suitable for administration by inhalation, by injection, orally, or intranasally.

Inhalable preparations include inhalable powders, propellant-containing metering aerosols or propellant-free inhalable formulations.

The present invention is also directed to a device which may be a single- or multi-dose dry powder inhaler, a metered dose inhaler or a soft mist nebulizer comprising a compound of formula (I) or (I').

The invention is also directed to a kit comprising the pharmaceutical compositions of compounds of formula (I) or (I') alone or in combination with or in admixture with one or more pharmaceutically acceptable carriers and/or excipients, and a device which may be a single- or multi-dose dry powder inhaler, a metered dose inhaler, or a soft mist nebulizer.

Advantageously, the compounds of formula (I) or (I') are administered at a dosage of 0.001 to 1000 mg/day, preferably 0.1 to 500 mg/day.

When they are administered by inhalation route, the dosage is advantageously 0.01 to 20 mg/day, preferably 0.1 to 10 mg/day.

The compounds of formula (I) or (I'), alone or combined with other active ingredients, are administered for the prevention and/or treatment of any obstructive respiratory disease such as asthma, chronic bronchitis, and chronic obstructive pulmonary disease (COPD).

The compounds of formula (I) or (I') may be administered for the prevention and/or treatment of any disease wherein the decrease in the number, activity, and movement of inflammatory cells is implicated.

Examples of such diseases include: diseases involving inflammation such as asthma and other allergic disorders, COPD, acute rhinitis; reverse acute transplant rejection and acute exacerbations of selected autoimmune disorders, graft-versus-host disease in bone-marrow transplantation; autoimmune disorders such as rheumatoid and other arthritis; skin conditions such as systemic lupus erythematosus, systemic dermatomyositis, psoriasis; inflammatory bowel disease, inflammatory ophthalmic diseases, autoimmune hematologic disorders, and acute exacerbations of multiple sclerosis; kidney, liver, heart, and other organ transplantation; Behçet's acute ocular syndrome, endogenous uveitis, atopic dermati tis, and nephrotic syndrome; Hodgkin's disease and non-Hodgkin's lymphoma, multiple myeloma and chronic lymphocytic leukemia (CLL); autoimmune hemolytic anemia and thrombocytopenia associated with CLL; leukemia and malignant lymphoma.

Preferably the compounds of formula (I) or (I') are administered for the prevention and/or treatment of respiratory diseases such as from mild to acute severe conditions of asthma and COPD.

Preferred compounds of the invention are reported below:

| Compound | Chemical Name |
| --- | --- |
| Compound 7 | Acetic acid 2-[(4aS,4bR,5S,6aS,6bS,9aR,10aS,10bS,12S)-4b,12-difluoro-5-hydroxy-4a,6a-dimethyl-8-(3-methyl-benzyl)-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| Compound 8 | Acetic acid 2-[(4aS,4bR,5S,6aS,6bS,9aR,10aS,10bS,12S)-4b,12-difluoro-5-hydroxy-4a,6a-dimethyl-8-(4-methyl-benzyl)-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| Compound 9 | (4aS,4bR,5S,6aS,6bS,9aR,10aS,10bS,12S)-4b,12-Difluoro-5-hydroxy-6b-(2-hydroxy-acetyl)-4a,6a-dimethyl-8-(3-methyl-benzyl)-4b,5,6,6a,6b,7,8,9,9a,10,10a,10b,11,12-tetradecahydro-4aH-8-aza-pentaleno[2,1-a]phenanthren-2-one |
| Compound 10 | (4aS,4bR,5S,6aS,6bS,9aR,10aS,10bS,12S)-4b,12-Difluoro-5-hydroxy-6b-(2-hydroxy-acetyl)-4a,6a-dimethyl-8-(4-methyl-benzyl)-4b,5,6,6a,6b,7,8,9,9a,10,10a,10b,11,12-tetradecahydro-4aH-8-aza-pentaleno[2,1-a]phenanthren-2-one |
| Compound 11 | Acetic acid 2-((4aS,4bR,5S,6aS,6bS,9aR,10aS,10bS,12S)-4b,12-difluoro-5-hydroxy-4a,6a-dimethyl-2-oxo-8-quinolin-2-ylmethyl-2,4b,5,6,6a,7,8,9,9a,10,10a,10b,11,12-tetradecahydro-4aH-8-aza-pentaleno[2,1-a]phenanthren-6b-yl)-2-oxo-ethyl ester |
| Compound 12 | (4aS,4bR,5S,6aS,6bS,9aR,10aS,10bS,12S)-4b,12-Difluoro-5-hydroxy-6b-(2-hydroxy-acetyl)-4a,6a-dimethyl-8-quinolin-2-ylmethyl-4b,5,6,6a,6b,7,8,9,9a,10,10a,10b,11,12-tetradecahydro-4aH-8-aza-pentaleno[2,1-a]phenanthren-2-one |
| Compound 13 | Acetic acid 2-((4aS,4bR,5S,6aS,6bS,9aR,10aS,10bS,12S)-8-Benzo[b]thiophen-2-ylmethyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester |
| Compound 14 | Acetic acid 2-[(4aS,4bR,5S,6aS,6bS,9aR,10aS,10bS,12S)-4b,12-difluoro-5-hydroxy-4a,6a-dimethyl-2-oxo-8-(3-phenyl-propyl)-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| Compound 15 | (4aS,4bR,5S,6aS,6bS,9aR,10aS,10bS,12S)-8-Benzo[b]thiophen-2-ylmethyl-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| Compound 16 | Acetic acid 2-((4aS,4bR,5S,6aS,6bS,9aR,10aS,10bS,12S)-4b,12-difluoro-5-hydroxy-4a,6a-dimethyl-2-oxo-8-quinolin-2-yl-2,4b,5,6,6a,7,8,9,9a,10,10a,10b,11,12-tetradecahydro-4aH-8-aza-pentaleno[2,1-a]phenanthren-6b-yl)-2-oxo-ethyl ester |
| Compound 17 | (4aS,4bR,5S,6aS,6bS,9aR,10aS,10bS,12S)-4b,12-Difluoro-5-hydroxy-6b-(2-hydroxy-acetyl)-4a,6a-dimethyl-8-quinolin-2-yl-4b,5,6,6a,6b,7,8,9,9a,10,10a,10b,11,12-tetradecahydro-4aH-8-aza-pentaleno[2,1-a]phenanthren-2-one |
| Compound 18 | (4aS,4bR,5S,6aS,6bS,9aR,10aS,10bS,12S)-8-(1H-Benzoimidazol-2-yl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| Compound 19 | Acetic acid 2-[(4aS,4bR,5S,6aS,6bS,9aR,10aS,10bS,12S)-8-(1H-benzoimidazol-2-yl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| Compound 20 | (4aS,4bR,5S,6aS,6bS,9aR,10aS,10bS,12S)-4b,12-Difluoro-5-hydroxy-4a,6a-dimethyl-2-oxo-8-(3-phenyl-propyl)-2,4b,5,6,6a,7,8,9,9a,10,10a,10b,11,12-tetradecahydro-4aH-8-aza-pentaleno[2,1-a]phenanthrene-6b-carboxylic acid fluoromethyl ester |
| Compound 21 | (4aS,4bR,5S,6aS,6bS,9aR,10aS,10bS,12S)-4b,12-Difluoro-5-hydroxy-4a,6a-dimethyl-2-oxo-8-(3-phenyl-propyl)-2,4b,5,6,6a,7,8,9,9a,10,10a,10b,11,12-tetradecahydro-4aH-8-aza-pentaleno[2,1-a]phenanthrene-6b-carboxylic acid cyanomethylester |
| Compound 22 | Acetic acid 2-[(4aS,4bR,5S,6aS,6bS,9aR,10aS,10bS,12S)-8-(4-chloro-phenyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| Compound 23 | (4aS,4bR,5S,6aS,6bS,9aR,10aS,10bS,12S)-8-(4-Chloro-phenyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |

-continued

| Compound | Chemical Name |
| --- | --- |
| Compound 24 | (4aS,4bR,5S,6aS,6bS,9aR,10aS,10bS,12S)-8-(3-Chloro-phenyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| Compound 26 | (4aS,4bR,5S,6aS,6bS,9aR,10aS,10bS,12S)-4b,12-Difluoro-5-hydroxy-4a,6a-dimethyl-2-oxo-8-phenyl-2,4b,5,6,6a,7,8,9,9a,10,10a,10b,11,12-tetradecahydro-4aH-8-aza-pentaleno[2,1-a]phenanthrene-6b-carboxylic acid |
| Compound 27 | (4aS,4bR,5S,6aS,6bS,9aR,10aS,10bS,12S)-4b,12-Difluoro-5-hydroxy-4a,6a-dimethyl-2-oxo-8-phenyl-2,4b,5,6,6a,7,8,9,9a,10,10a,10b,11,12-tetradecahydro-4aH-8-aza-pentaleno[2,1-a]phenanthrene-6b-carbothioic acid S-fluoromethyl ester |
| Compound 32 | (4aS,4bR,5S,6aS,6bS,9aR,10aS,10bS,12S)-4b,12-Difluoro-6b-(2-fluoro-acetyl)-5-hydroxy-4a,6a-dimethyl-8-phenyl-4b,5,6,6a,6b,7,8,9,9a,10,10a,10b,11,12-tetradecahydro-4aH-8-aza-pentaleno[2,1-a]phenanthren-2-one |

The compounds of formula (I') may be prepared according to different routes, described in the following Scheme, depending on the nature of the substituents $R_1$ and $R_2$.

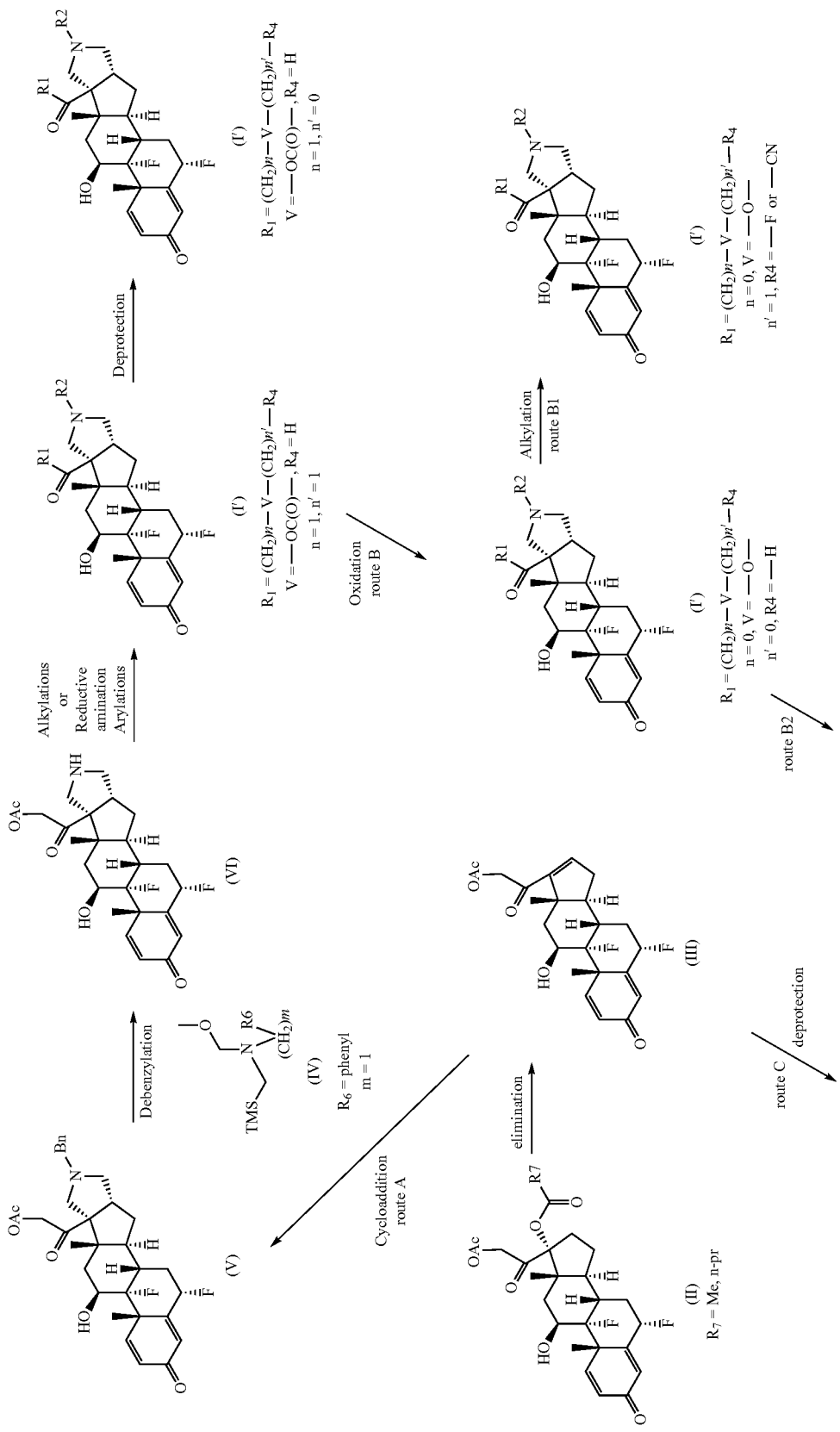

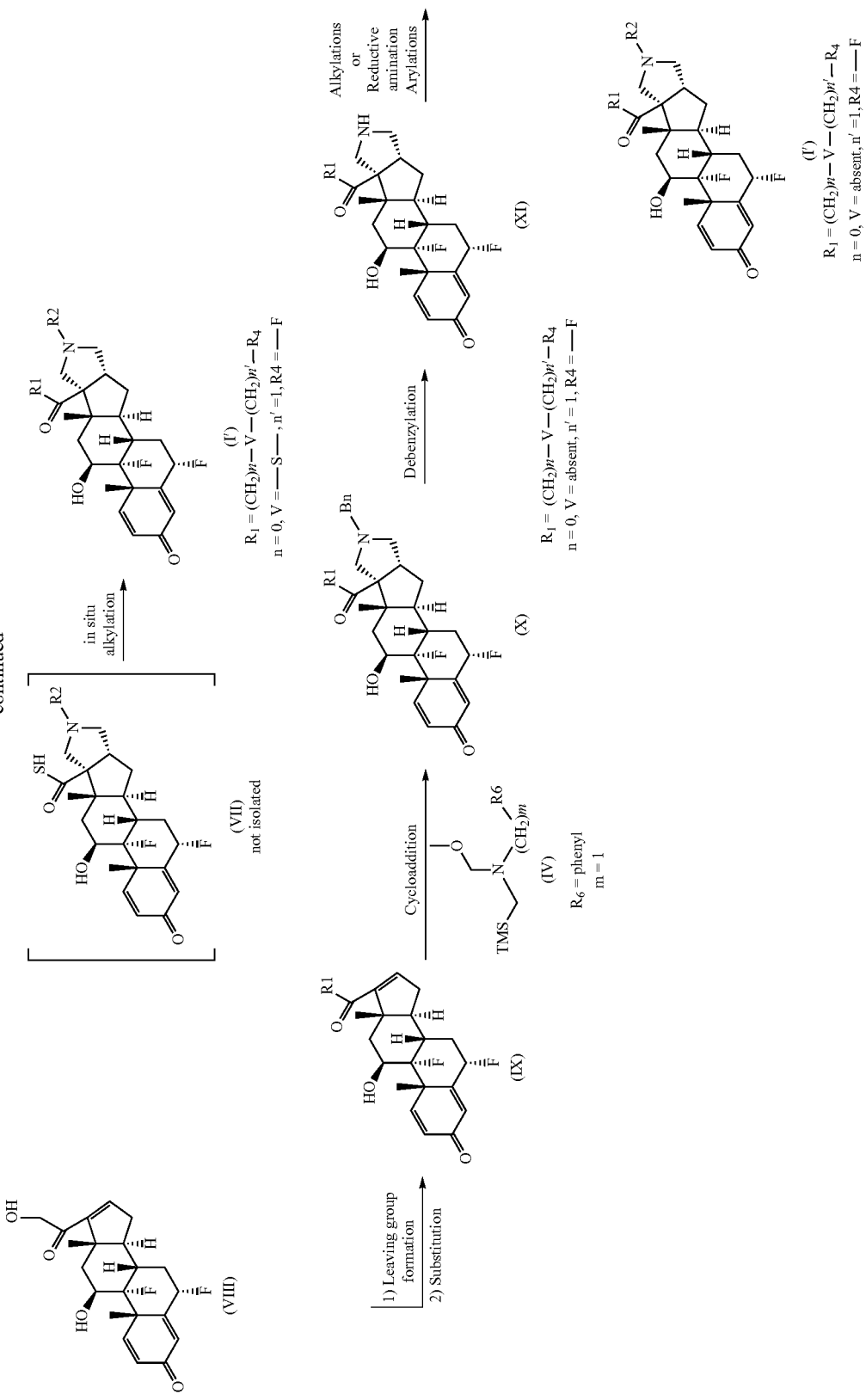

Compounds of formula (I') wherein $R_1$ is $(CH_2)_n$—V—$(CH_2)_{n'}$—$R_4$, wherein n=1, n'=0, V is —O— and $R_4$ is —H, can be prepared by a four steps procedure following Route A, starting from the reaction of a compound of formula (III) with N-benzyl-N-(trimethylsilylmethyl)aminomethyl ether (compound (IV), which is an azomethine ylide precursor, wherein m=1 and $R_6$=phenyl) under the 1,3-dipolar cycloaddition (1,3-DC) conditions of unsaturated compounds and azomethine ylides. The ylide is generated in situ from the suitable precursor, e.g. compound (IV). The reaction involves the use of 1 to 7 equivalents of azomethine ylide precursor, and it is usually performed in a high boiling point solvent such as THF, dioxane, toluene, or xylene. The reaction usually proceeds in a range of temperature from 50 to 150° C. over a period of 1 to 5 hours and may be promoted by an acid such as trifluoroacetic acid, trimethylsilyl iodide, or trimethylsilyl trifluoromethanesulfonate. Sodium, potassium, or cesium fluoride could also be effective in catalyzing the reaction. Azomethine ylide precursor (IV) is commercially available or can be prepared as described in the literature, for example following the procedure described in *J. Chem. Soc., Perkin Trans.*, 1, 1998, p 3867-3872, which is incorporated herein by reference in its entirety. Compounds of general formula (III) may be conveniently prepared according to standard procedures reported in the literature. For instance they may be prepared by treatment of compounds of general formula (II) with a base such as potassium acetate. This reaction is usually performed in a suitable polar solvent (e.g. dimethylformamide (DMF)) and typically proceeds at a temperature range from 80 to 110° C., over a period of 0.5 to 4 hours. Compounds of formula (II) are commercially available or may be readily prepared from known compounds by known methods (see *J. Med. Chem.*, 1982, 25, 1492-1495, which is incorporated herein by reference in its entirety). The benzyl group can be removed by chemical dealkylation of tertiary amines with acyl chlorides, phosgene analogues, or preferably chloroformates such as vinylchloroformate. The reaction is usually performed in a suitable solvent such as dichloromethane (DCM), tetrahydrofuran (THF), or acetonitrile at temperature range from room temperature (RT) to 60° C. The reaction requires the presence of a base, such as alkali carbonates or bicarbonates or an organic base such as pyridine, and it is usually completed in a time of from 0.5 to 2 hours. The carbamate obtained from the first step of the reaction is deprotected under known conditions (see Wiley-VCH; Wuts, Peter G. M./Greene, Theodora W., Greene's Protective Groups in Organic Synthesis, 1999, p. 503 and following, which is incorporated herein by reference in its entirety) affording compound (VI). Compound (VI) can be easily further functionalized to obtain compounds of general formula (I').

In fact, aryl or heteroaryl groups can be introduced at the N atom of the pyrrolidine ring of compound (VI) by following described procedures for the N arylation of pyrrolidines. Compound of formula (VI) can be reacted with aryl boronic acids under metal catalyzed arylation conditions. The reaction is promoted by copper (I or II) salts, nickel(II) phosphine complexes, and palladium complexes, and often a base such as sodium or potassium terbutylate or triethylamine (TEA) is required. The reaction occurs in a solvent such as DMF, dimethylacetamide (DMA), acetonitrile, dioxane, THF, toluene, dichloromethane (DCM), or N-methylpyrrolidone (NMP) at a temperature range from 20 to 200° C. by conventional thermal heating or by microwaves. In some cases, the reaction can occur by simple heating, from 20 to 150° C., of a solution of compound (VI) and a suitable aryl or heteroaryl derivative, such as halides or trifluoromethane sulfonates (triflate), in a solvent such as ethanol, THF, acetonitrile, DMF, DMA, dioxane, or NMP for a period of time from 0.5 to 24 hours. Alternatively, this compound can be prepared by reacting compound (VI) with a benzyne. This very reactive species can be generated in situ from a suitable precursor following methods described in the literature. A valid protocol involves the treatment of 2-trimethylsilyl-phenyl trifluoromethane sulfonates with cesium fluoride. The reaction occurs at RT in a polar solvent such as acetonitrile, and it is completed over a period from 1 to 72 hours. In the case the benzyne precursor features substituents on the benzene ring, the reaction can lead to a mixture of two regioisomers.

The alkylation of compound (VI) can be performed by applying the conditions for the alkylation of pyrrolidines. The reaction involves the use of alkyl halides, methane sulfonates, tosylates, or other alkyl derivatives suitable for amine alkylation and requires the presence of a base such as TEA, DIPEA, or pyridine for completion. It proceeds at a temperature from RT to 100° C. over 1 to 48 hours in a suitable solvent such as DCM, THF, acetonitrile, or DMF. The presence of sodium or potassium iodide can in some cases accelerate the reaction rate. The same class of derivatives can be obtained by reacting compound (VI) under reductive amination reaction conditions with a suitable aldehyde in a solvent such as acetonitrile. The imine intermediate is usually in situ reduced by treatment with reducing agents, such as formic acid and its salts at a temperature range from 70 to 150° C., over 10-30 minutes.

In all cases, the obtained products feature an acetoxy moiety on the side chain position at 6b of the steroid scaffold. This moiety can be easily hydrolyzed by treatment with a base such as LiOH, NaOH, KOH, or $K_2CO_3$ solid or dissolved in water, in organic solvents such as methanol, ethanol, or THF or alternatively with an aqueous acid solution (for example HCl) in a suitable organic solvent such as THF or dioxane at 40 to 80° C. over a period of 1 to 8 hours.

Route B—reaction of compounds of general formula (I') wherein $R_1$ is $(CH_2)_n$—V—$(CH_2)_{n'}$—$R_4$, wherein n=n'=1, V is —OC(O)— and $R_4$ is —H, under well known oxidation conditions to afford the compounds of general formula (I') wherein $R_1$ is $(CH_2)_n$—V—$(CH_2)_{n'}$—$R_4$, wherein n=n'=0, V is —O— and $R_4$ is —H. This reaction is usually performed in open air at RT over a period of 12 to 48 hours, in a suitable solvent such as THF or dioxane in the presence of an aqueous solution of an inorganic base, such as for example sodium or potassium hydroxide.

Route B1—Conversion of the compounds of general formula (I') wherein $R_1$ is $(CH_2)_n$—V—$(CH_2)_{n'}$—$R_4$, wherein n=n'=0, V is —O— and $R_4$ is —H, into compounds of general formula (I') wherein $R_1$ is $(CH_2)_n$—V—$(CH_2)_{n'}$—$R_4$, wherein n=0 and n'=1, V is —O— and $R_4$ is fluorine or —CN, can be obtained by treating the acid of general formula (I') wherein $R_1$ is $(CH_2)_n$—V—$(CH_2)_{n'}$—$R_4$, wherein n=n'=0, V is —O— and $R_4$ is —H, with an alkylating reagent such as bromofluoromethane or bromoacetonitrile in a suitable solvent such as DMF, at RT, in the presence of an inorganic base such as sodium carbonate over a period of 1 to 48 hours. These reactions are carried out as described in the literature for the synthesis of similar compounds and are well known.

Route B2—Conversion of acids of formula (I') wherein $R_1$ is $(CH_2)_n$—V—$(CH_2)_{n'}$—$R_4$, wherein n=n'=0, V is —O— and $R_4$ is —H, into compounds of general formula (I') wherein $R_1$ is $(CH_2)_n$—V—$(CH_2)_{n'}$—$R_4$, wherein n=0, n'=1, V is —S—, $R_4$ is fluorine, derived from reaction of acid (I') with for example carbonyldiimidazole or N-[(dimethylamino)-1H-1,2,3-triazolo[4,5-b]pyridine-1-ylmethylene]-N-methylmethanaminium hexafluorophosphate N-oxide (HATU), followed by reaction with the sodium salt of thioacetic acid or with sodium hydrogen sulfide. The reaction is usually performed by adding the solution of the preformed salt in the reaction solvent to the solution of the activated acid, at a temperature ranging from 0 to 20° C. The thioacid compounds of formula (VII) readily formed is in situ reacted with an alkylating reagent, such as bromofluoromethane, leading to thioesters of general formula (I').

Route C—In another embodiment of the present invention, compounds of formula (I') wherein $R_1$ is $(CH_2)_n$—V—$(CH_2)_{n'}$—$R_4$, wherein n=0, V is absent, n'=1, $R_4$ is halide can be prepared by a five steps procedure, starting from the conversion of the hydroxyl group of 2-hydroxy acetyl moiety at position 6b of compound (VIII) into a leaving group (LG) using methanesulfonyl chloride or p-toluenesulfonyl chloride (see March, "Advanced Organic Chemistry", Wiley-Interscience, 2001, which is incorporated herein by reference in its entirety), in a suitable solvent, for example acetonitrile in the presence of an organic base such as DIPEA. This reaction is usually performed at RT over a period of 1 to 24 hours, and the obtained activate intermediates are submitted to the displacement of the LG by using a nucleophile such as a halide salt to obtain compounds of general formula (IX). This displacement is usually performed in situ for example by the addition of TBAF and/or potassium fluoride and refluxing the reaction mixture over a period of 24-48 hours. The compounds of formula (VIII) may be prepared hydrolyzing the compounds of formula (III). This reaction is preferably carried out by subjecting compounds (III) to the action of an enzyme, such as for example immobilized Lipase from *Candida Antarctica* (Sigma Aldrich) (see Tetrahedron 1994, Vol. 50, No. 46, 13165-13172, which is incorporated herein by reference in its entirety).

The third step is the 1-3 dipolar cycloaddition reaction of compounds of general formula (IX) with compound (IV) performed as described above (Route A) to yield compounds of general formula (X). In particular, a compound of formula (IX) can react with N-benzyl-N-(trimethylsilylmethyl)aminomethyl ether (i.e. compound (IV), which is an azomethine ylide precursor, wherein m=1 and $R_6$=phenyl) under the 1,3-dipolar cycloaddition (1,3-DC) conditions of unsaturated compounds and azomethine ylides. The ylide is generated in situ from the suitable precursor, e.g. compound (IV). The reaction involves the use of 1 to 7 equivalents of azomethine ylide precursor, and it is usually performed in a high boiling point solvent such as dioxane. The reaction usually proceeds in a range of temperature from 50 to 150° C. over a period of 1-5 hours and may be promoted by an acid such as trifluoroacetic acid.

The fourth step is the benzyl group removal of intermediate (X) by chemical dealkylation of tertiary amines with a chloroformate such as vinylchloroformate as described above (Route A) to obtain compound of formula (XI). The reaction is usually performed in a suitable solvent such as dichloromethane (DCM), tetrahydrofuran (THF), or acetonitrile at temperature range from RT to 60° C. The reaction requires the presence of a base such as alkali carbonates or bicarbonates or an organic base such as pyridine and it is usually completed over a time range from 0.5 to 2 hours. The carbamate obtained from the first step of the reaction is deprotected under known conditions (Wiley-VCH; Wuts, Peter G. M./Greene, Theodora W. Greene's Protective Groups in Organic Synthesis, 1999, p. 503 and following, which is incorporated herein by reference in its entirety) affording intermediate (XI). The last step is the functionalization of intermediate (XI) by arylation, alkylation, or reductive amination reactions as previously described for compound (VI) (Route A) yielding compounds of general formula (I'). In particular, aryl or heteroaryl groups can be introduced at the N atom of the pyrrolidine ring of compound (XI) by following described procedures for the N arylation of pyrrolidines. The compound of formula (XI) can be reacted with aryl boronic acids under metal catalyzed arylation conditions. The reaction is promoted by copper (I or II) salts, nickel(II) phosphine complexes, and palladium complexes, and often a base such as sodium or potassium terbutylate or triethylamine (TEA) is required. The reaction occurs in a solvent such as DMF, dimethylacetamide (DMA), acetonitrile, dioxane, THF, toluene, dichloromethane (DCM), or N-methylpyrrolidone (NMP) at a temperature range from 20 to 200° C. by conventional thermal heating or by microwaves. In some cases the reaction can occur by simple heating, from 20 to 150° C., of a solution of compound (XI) and a suitable aryl or heteroaryl derivative, such as halides or trifluoromethane sulfonates (triflate), in a solvent such as ethanol, THF, acetonitrile, DMF, DMA, dioxane, or NMP for a period of time from 0.5 to 24 hours. Alternatively this compound can be prepared by reacting compound (XI) with a benzyne. This very reactive species can be generated in situ by the treatment of 2-trimethylsilyl-phenyl trifluoromethane sulfonates with cesium fluoride. The reaction occurs at RT in a polar solvent such as acetonitrile and it is completed over a period from 1 to 72 hours. In the case the benzyne precursor features substituents on the benzene ring, the reaction can lead to a mixture of two regioisomers.

The alkylation of compound (XI) can be performed applying the conditions for the alkylation of pyrrolidines. The reaction involves the use of alkyl halides, methane sulfonates, tosylates, or other alkyl derivatives suitable for amine alkylation and requires the presence of a base such as TEA, DIPEA, or pyridine for completion. It proceeds at a temperature from RT to 100° C. over 1 to 48 hours in a suitable solvent such as DCM, THF, acetonitrile, or DMF. The presence of sodium or potassium iodide can in some cases accelerate the reaction rate. The same class of derivatives can be obtained by reacting compound (XI) under reductive amination reaction conditions with a suitable aldehyde in a solvent such as acetonitrile. The imine intermediate is usually in situ reduced by treatment with reducing agents, such as formic acid and its salts at a temperature range from 70 to 150° C., over 10 to 30 minutes.

Other features of the invention will become apparent in the course of the following descriptions of exemplary embodiments which are given for illustration of the invention and are not intended to be limiting thereof.

EXAMPLES

Example 1

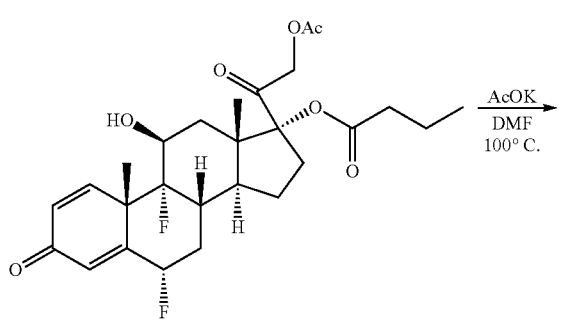

1

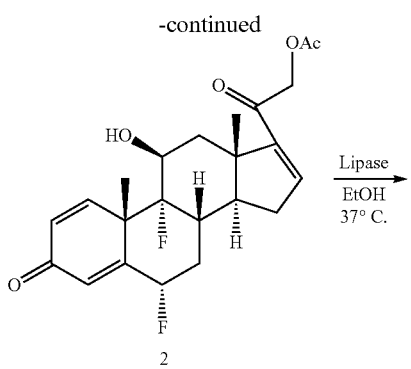

chromatography on silica gel, in gradient elution from DCM/AcOEt 90:10 to DCM/AcOEt 50:50, to afford the title compound (1.62 g, 70.6% yield).

$^1$H NMR (300 MHz, DMSO-d$_6$): ppm 7.29 (dd, 1H), 6.87 (dd, 1H), 6.29 (dd, 1H), 6.09-6.17 (m, 1H), 5.67 (dddd, 1H), 5.53 (dd, 1H), 4.77 (t, 1H), 4.44 (dd, 1H), 4.26 (dd, 1H), 4.04-4.15 (m, 1H), 2.56-2.79 (m, 1H), 2.39 (dd, 1H), 2.25-2.35 (m, 2H), 2.09-2.25 (m, 1H), 1.76 (td, 1H), 1.55-1.66 (m, 2H), 1.53 (s, 3H), 1.17 (s, 3H)

LC-MS (ESI POS): 379.2 (MH+)

Example 2

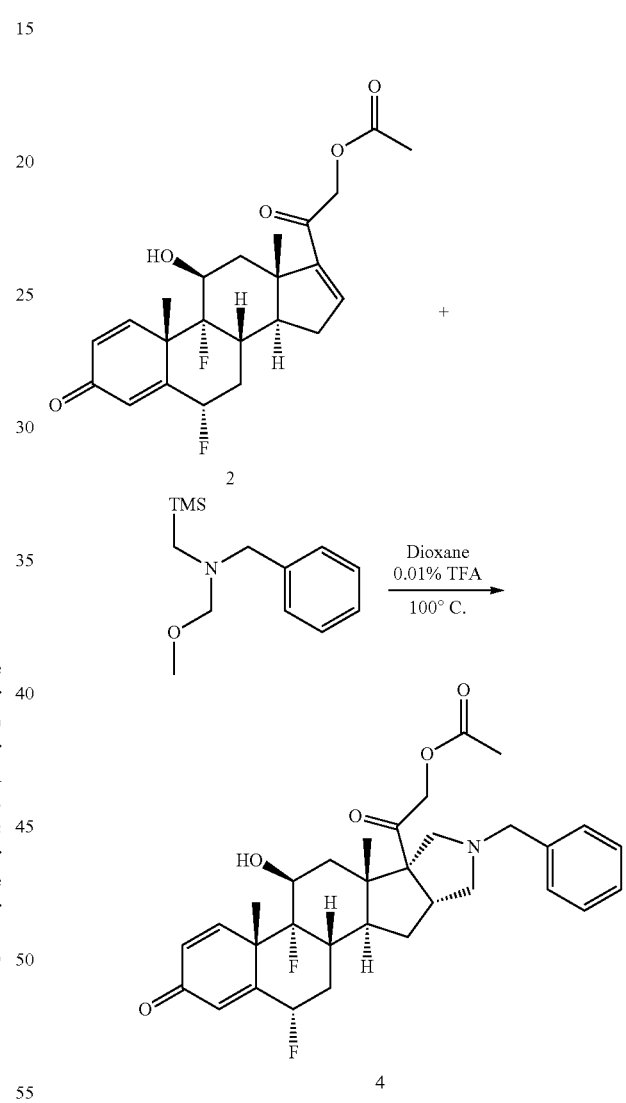

Preparation of Acetic acid 2-((6S,8S,9R,10S,11S,13S,14S)-6,9-difluoro-11-hydroxy-10,13-dimethyl-3-oxo-6,7,8,9,10,11,12,13,14,15-decahydro-3H-cyclopenta[a]phenanthren-17-yl)-2-oxo-ethyl ester (intermediate 2)

To a solution of butyric acid (6S,8S,9R,10S,11S,13S,14S,17R)-17-(2-acetoxyacetyl)-6,9-difluoro-11-hydroxy-10,13-dimethyl-3-oxo-7,8,9,10,11,12,13,14,15,16,17-dodecahydro-3H-cyclopenta[a]phenanthren-17-yl ester (intermediate 1) (2.48 g, 4.88 mmol) in anhydrous DMF (60 ml), under nitrogen atmosphere, potassium acetate (3.83 g, 39.0 mmol) was added, and the reaction mixture was stirred at 100° C. for 1.5 hours. The reaction mixture was cooled to RT and then poured into ice and brine (200 ml), and the aqueous layer was extracted with AcOEt (3×150 ml). The combined organic extracts were washed with water and brine, dried over Na2SO4 and concentrated to afford 2.55 g of crude title compound which was used in the next step without further purification.

$^1$H NMR (300 MHz, DMSO-d$_6$): δ ppm 7.29 (dd, 1H), 6.99 (dd, 1H), 6.29 (dd, 1H), 5.98-6.15 (m, 1H), 5.68 (dddd, 1H), 5.56 (dd, 1H), 5.10 (d, 1H), 4.92 (d, 1H), 3.98-4.23 (m, 1H), 2.56-2.83 (m, 1H), 2.26-2.44 (m, 3H), 2.14-2.26 (m, 1H), 2.09 (s, 3H), 1.71-1.87 (m, 1H), 1.55-1.65 (m, 2H), 1.53 (s, 3H), 1.15 (s, 3H)

LC-MS (ESI POS): 421.2 (MH+)

Preparation of (6S,8S,9R,10S,11S,13S,14S)-6,9-Difluoro-11-hydroxy-17-(2-hydroxy-acetyl)-10,13-dimethyl-6,7,8,9,10,11,12,13,14,15-decahydro cyclopenta[a]phenanthren-3-one (intermediate 3)

To a solution of intermediate 2 (2.55 g, 6.06 mmol) in ethanol (100 ml), *Candida antarctica* Lipase (2 U/mg) (510 mg, 6.06 mmol) was added, and the reaction mixture was stirred at 37° C. overnight. The reaction mixture was filtered, washing with methanol, and the residue was purified by flash Preparation of Acetic acid 2-((4aS,4bR,5S,6aS,6bS,9aR,10aS,10bS,12S)-8-benzyl-4b,12-difluoro-5-hydroxy-4a,6a-dimethyl-2-oxo-2,4b,5,6,6a,7,8,9,9a,10,10a,10b,11,12-tetradecahydro-4aH-8-azapentaleno[2,1-a]phenanthren-6b-yl)-2-oxo-ethyl ester (intermediate 4)

In a nitrogen atmosphere, a mixture of intermediate 2 (3.63 g, 8.63 mmol) and N-benzyl-N-(trimethylsilylmethyl)ami nomethyl ether (10.25 g, 43.2 mmol) in dioxane (50 ml) was stirred under nitrogen in a preheated bath at 100° C. for 2 hours. The solvent was evaporated, and the residue was triturated several times with petroleum ether to give a pale yellow solid. The solid was purified by silica gel chromatography (AcOEt/petroleum ether 1:1) to yield the title intermediate (4.47 g, 94% yield).

$^1$H NMR (300 MHz, DMSO-d$_6$) δ ppm 6.79-7.68 (m, 6H), 6.29 (dd, 1H), 6.13 (s, 1H), 5.48-5.82 (m, 1H), 5.36-5.46 (m, 1H), 4.95 (d, 1H), 4.79 (d, 1H), 4.01-4.24 (m, 1H), 3.47 (s, 1H), 3.03-3.21 (m, 1H), 2.83-2.98 (m, 1H), 2.54-2.61 (m, 1H), 2.24-2.46 (m, 4H), 2.11 (s, 3H), 1.94-2.10 (m, 2H), 1.85 (d, 1H), 1.52-1.74 (m, 3H), 1.49 (s, 3H), 1.28-1.43 (m, 1H), 0.92 (s, 3H)

LC-MS (ESI POS): 554.2 (MH+)

Example 3

Preparation of (4aS,4bR,5S,6aS,6bS,9aR,10aS,10bS, 12S)-6b-(2-Acetoxy-acetyl)-4b,12-difluoro-5-hydroxy-4a,6a-dimethyl-2-oxo-2,4b,5,6,6a,6b,7,9,9a, 10,10a,10b,11,12-tetradecahydro-4aH-8-aza-pentaleno[2,1-a]phenanthrene-8-carboxylic acid vinyl ester (intermediate 5)

Intermediate 4 (1.95 g, 3.52 mmol) and NaHCO$_3$ (0.592 g, 7.04 mmol) were dissolved in acetonitrile (30 ml), and then vinyl chloroformate (0.599 ml, 7.04 mmol) was added. The reaction mixture was warmed at 50° C. for 2 hours. The solution was partitioned between AcOEt and brine. The organic phase was separated, while the aqueous solution was extracted with AcOEt. The combined organic phases were dried over Na$_2$SO$_4$ and then evaporated to give a residue that was purified by silica gel column chromatography, eluting with Petroleum Ether/AcOEt 6:4 to 4:6, leading to pure title intermediate (1.1 g, 58.5% yield).

LC-MS (ESI POS): 534.1 (MH+)

Preparation of Acetic acid 2-((4aS,4bR,5S,6aS,6bS, 9aR,10aS,10bS,12S)-4b,12-difluoro-5-hydroxy-4a, 6a-dimethyl-2-oxo-2,4b,5,6,6a,7,8,9,9a,10,10a,10b, 11,12-tetradecahydro-4-aH-8-aza-pentaleno[2,1-a] phenanthren-6b-yl)-2-oxo-ethyl ester hydrochloride (intermediate 6)

Intermediate 5 (1.0 g, 1.874 mmol) was dissolved in dioxane (3 ml), and then HCl 4.0 M in dioxane (5 ml, 1.874 mmol) was added. The solution was stirred at RT for 2 hours, and then the solvent was evaporated, and the residue was dried under vacuum for 1 hour. The solid was then dissolved in methanol and warmed at 40° C. for 1 hour. Methanol was evaporated and the residue was triturated with diethyl ether to give the title intermediate (0.93 g, 99% yield).

LC-MS (ESI POS): 464.0 (MH+)

Example 4

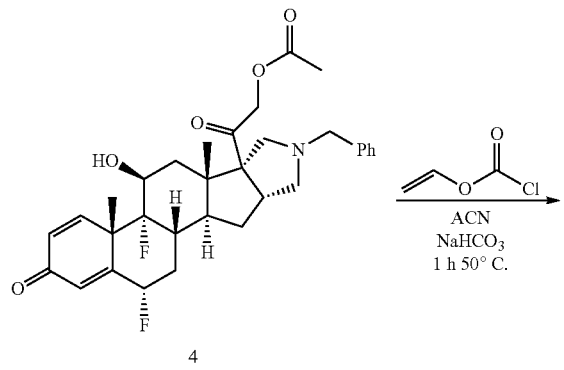

4

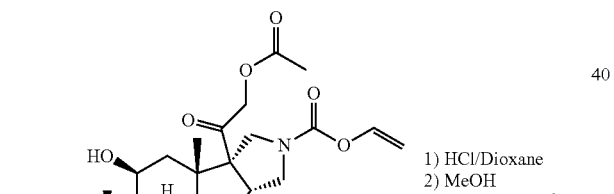

5

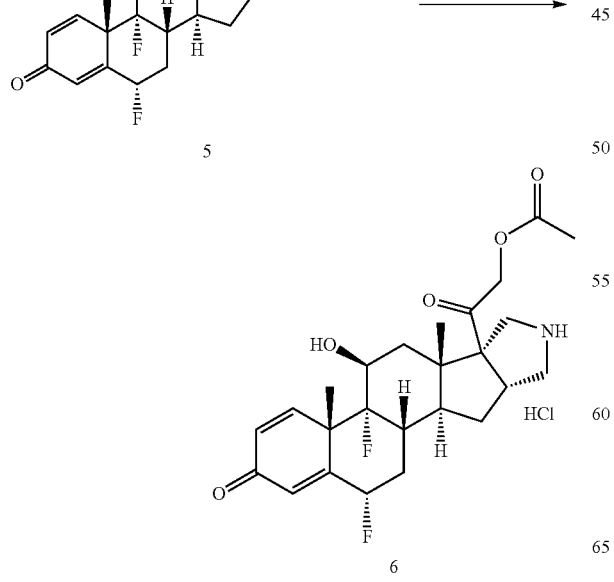

6

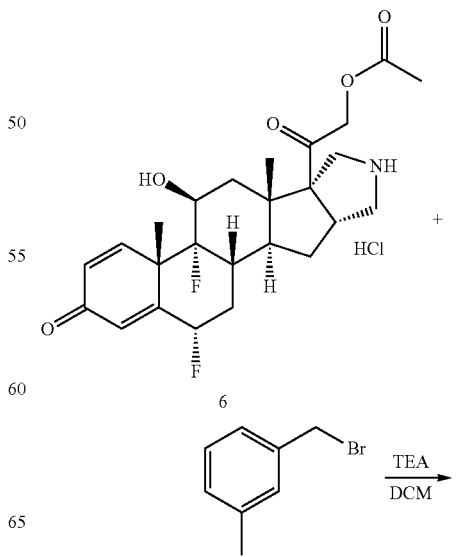

6

Example 5

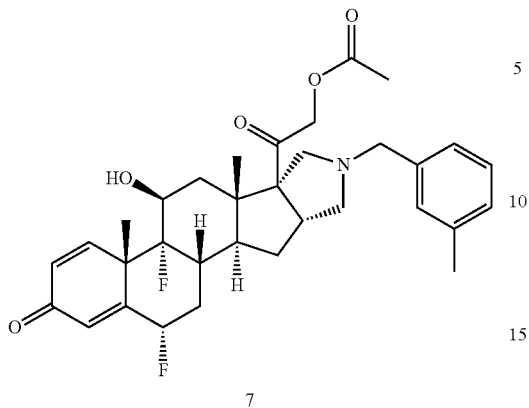

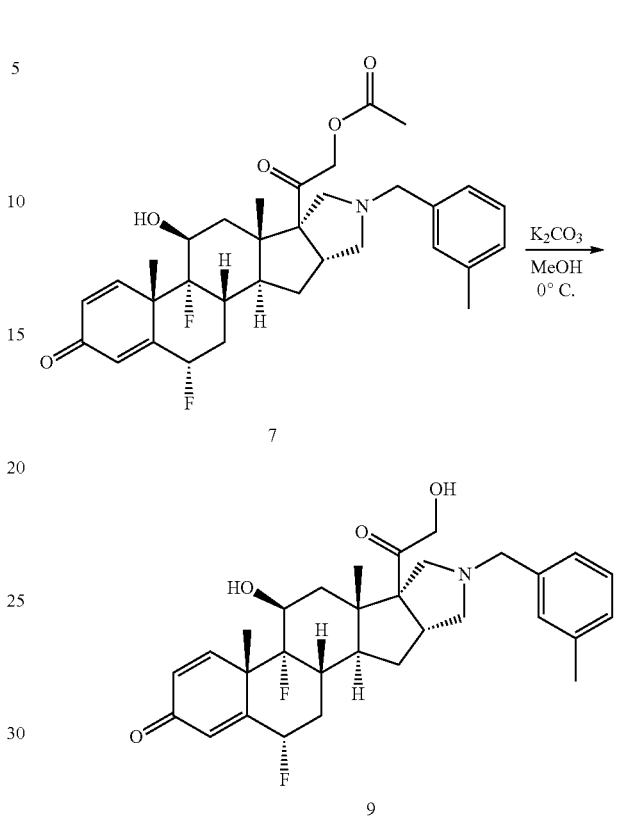

Preparation of Acetic acid 2-[(4aS,4bR,5S,6aS,6bS, 9aR,10aS,10bS,12S)-4b,12-difluoro-5-hydroxy-4a, 6a-dimethyl-8-(3-methyl-benzyl)-2-oxo-2,4b,5,6,6a, 7,8,9,9a,10,10a,10b,11,12-tetradecahydro-4aH-8-aza-pentaleno[2,1-a]phenanthren-6b-yl]-2-oxo-ethyl ester (compound 7)

In a nitrogen atmosphere, intermediate 6 (200 mg, 0.400 mmol) was dissolved in DCM (5 ml), triethylamine (166 μL, 1.20 mmol) and 1-(chloromethyl)-3-methylbenzene (79 μL, 0.60 mmol) were added, and the mixture was heated at 40° C. for 2 hours and at RT for 16 hours. Then triethylamine (138 μL, 1.00 mmol) and 3-methylbenzyl bromide (54 μL, 0.40 mmol) were added to the mixture, and stirring was continued for 2 hours. The reaction mixture was partitioned between water and DCM, and the aqueous layer was extracted with DCM (3×15 mL), and the organic phase was collected and concentrated. The crude was purified by silica gel flash chromatography (eluent DCM/MeOH 99:1) to yield the title compound (130 mg, 57.2% yield).

LC-MS (ESI-POS): 568.3 MH+

Compound 8 in Table 1 was prepared as described in Example 4 for compound 7, by reacting intermediate 6 with the commercially available 4-methylbenzylbromide.

Preparation of (4aS,4bR,5S,6aS,6bS,9aR,10aS,10bS, 12S)-4b,12-Difluoro-5-hydroxy-6b-(2-hydroxy-acetyl)-4a,6a-dimethyl-8-(3-methyl-benzyl)-4b,5,6, 6a,6b,7,8,9,9a,10,10a,10b,11,12-tetradecahydro-4aH-8-aza-pentaleno[2,1-a]phenanthren-2-one (compound 9)

Compound 7 (130 mg, 0.229 mmol) was dissolved in MeOH (8 ml), and the mixture was degassed with nitrogen for

TABLE 1

| Compound | Structure | Yield | Analytical |
|---|---|---|---|
| 8 | 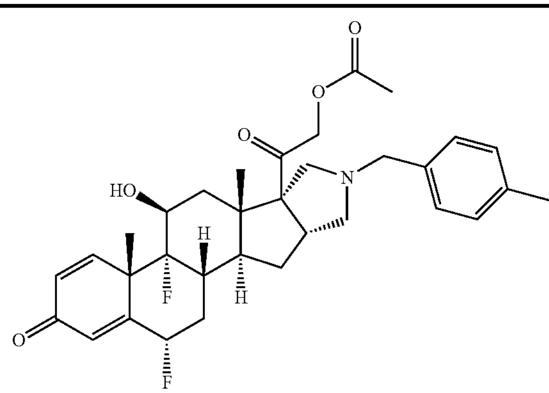 | 61% | LC-MS (ESI-POS): 568.3 MH+ |

15 minutes. After cooling to 0° C., K$_2$CO$_3$ (15.8 mg, 0.115 mmol) was added, and the mixture was stirred for 1 hour. The reaction mixture was partitioned between a 5% NaHCO$_3$ solution and AcOEt. The organic layer was separated, dried over Na$_2$SO$_4$, and concentrated. The crude was purified by silica gel flash chromatography (eluent DCM/MeOH 99:1 to 98:2) to give the title compound (91 mg, 76% yield).

$^1$H NMR (300 MHz, DMSO-d$_6$) δ ppm 7.25 (d, 1H), 7.09-7.21 (m, 1H), 6.92-7.06 (m, 3H), 6.29 (d, 1H), 6.13 (s, 1H), 5.45-5.81 (m, 1H), 5.40 (br. s., 1H), 4.83 (t, 1H), 4.06-4.28 (m, 3H), 3.33-3.53 (m, 3H), 3.15 (d, 1H), 2.84 (t, 1H), 2.34-2.48 (m, 2H), 2.19-2.34 (m, 1H), 2.24 (s, 3H), 1.94-2.14 (m, 2H), 1.77-1.89 (m, 1H), 1.42-1.77 (m, 3H), 1.49 (s, 3H), 1.35 (dd, 1H), 0.87 (s, 3H)

LC-MS (ESI POS): 526.30 MH+

[α]$_D^{25}$+81.0 (c 0.33, MeOH)

Compound 10 in Table 2 was prepared as described in Example 5 for compound 9, starting from compound 8.

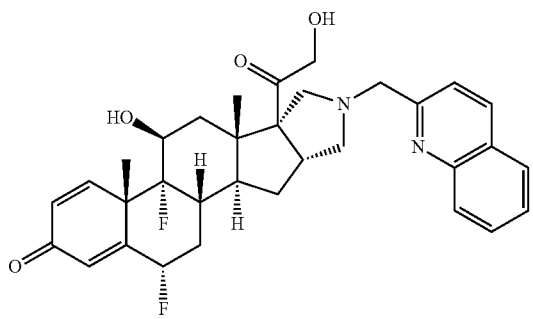

12

TABLE 2

| Compound | Structure | Yield | Analytical |
|---|---|---|---|
| 10 | 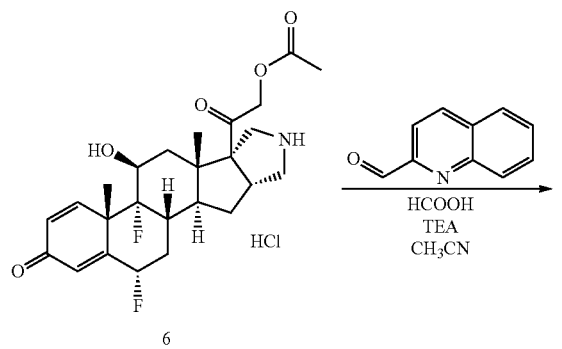 | 47% | $^1$H NMR (300 MHz, DMSO-d$_6$) δ ppm 7.25 (dd, 1 H), 7.08 (s, 4 H), 6.29 (dd, 1 H), 6.13 (s, 1 H), 5.48-5.83 (m, 1 H), 5.39 (dd, 1 H), 4.82 (t, 1 H), 4.22 (dd, 1 H), 4.11-4.17 (m, 1 H), 4.11 (dd, 1 H), 3.39 (s, 2 H), 3.05-3.21 (m, 1 H), 2.85 (t, 1 H), 2.55-2.69 (m, 2 H), 2.36 (d, 1 H), 2.26 (s, 3 H), 2.21-2.32 (m, 1 H), 1.92-2.12 (m, 2 H), 1.77-1.92 (m, 1 H), 1.51-1.76 (m, 3 H), 1.49 (s, 3 H), 1.34 (dd, 1 H), 0.86 (s, 3 H) LC-MS (ESI POS): 526.32 MH+ [α]$_D^{25}$ + 89.3 (c = 0.33, MeOH) |

Example 6

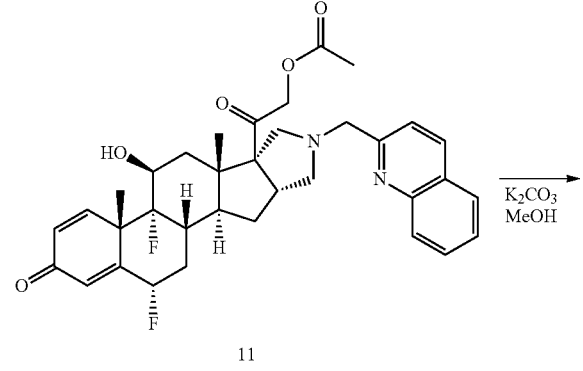

Preparation of Acetic acid 2-((4aS,4bR,5S,6aS,6bS, 9aR,10aS,10bS,12S)-4b,12-difluoro-5-hydroxy-4a, 6a-dimethyl-2-oxo-8-quinolin-2-ylmethyl-2,4b,5,6, 6a,7,8,9,9a,10,10a,10b,11,12-tetradecahydro-4aH-8-aza-pentaleno[2,1-a]phenanthren-6b-yl)-2-oxo-ethyl ester (compound 11)

A solution of intermediate 6 (200 mg, 0.400 mmol), quinoline-2-carbaldehyde (251 mg, 1.600 mmol), triethylamine (61 mL, 0.440 mmol) and formic acid (263 μL, 3.20 mmol), in acetonitrile (4 ml) is irradiated with microwaves (130° C., 20 minutes). The reaction mixture was partitioned between AcOEt and 5% NaHCO$_3$ solution. The organic layers were then washed with brine, dried over Na$_2$SO$_4$ and filtered. The solvent was evaporated and the crude was purified by silica gel chromatography (DCM/MeOH 99:1) to give compound 11 (132 mg, 54.6% yield).

LC-MS (ESI POS): 605.3 MH+

Preparation of 4aS,4bR,5S,6aS,6bS,9aR,10aS,10bS, 12S)-4b,12-Difluoro-5-hydroxy-6b-(2-hydroxy-acetyl)-4a,6a-dimethyl-8-quinolin-2-ylmethyl-4b,5, 6,6a,6b,7,8,9,9a,10,10a,10b,11,12-tetradecahydro-4aH-8-aza-pentaleno[2,1-a]phenanthren-2-one (compound 12)

The title compound was prepared from compound 11 (130 mg, 0.215 mmol) following the procedure described in Example 5 for the synthesis of compound 9. Compound 12 (68 mg, 56% yield) was obtained.

¹H NMR (300 MHz, DMSO-d₆) δ ppm 8.29 (d, 1H), 7.89-8.00 (m, 2H), 7.72 (ddd, 1H), 7.56 (ddd, 1H), 7.46 (d, 1H), 7.26 (dd, 1H), 6.30 (dd, 1H), 6.14 (s, 1H), 5.50-5.87 (m, 1H), 5.27-5.44 (m, 1H), 4.85 (t, 1H), 4.28 (dd, 1H), 4.14 (dd, 1H), 4.01-4.15 (m, 1H), 3.76 (s, 2H), 3.12-3.24 (m, 1H), 2.94 (t, 1H), 2.62 (d, 1H), 2.54-2.62 (m, 2H), 2.22-2.37 (m, 1H), 2.17 (dd, 1H), 2.01-2.13 (m, 1H), 1.78-1.93 (m, 1H), 1.52-1.78 (m, 3H), 1.49 (s, 3H), 1.39 (dd, 1H), 0.88 (s, 3H)

LC-MS (ESI POS): 563.35 MH+

$[\alpha]_D^{25}$ +76.1 (c 0.32, MeOH)

The compounds listed in Table 3 were prepared as described in Example 6 for compound 11, starting from intermediate 6 and the suitable commercially available aldehyde.

TABLE 3

| Compound | Structure | Yield | Analytical |
|---|---|---|---|
| 13 | 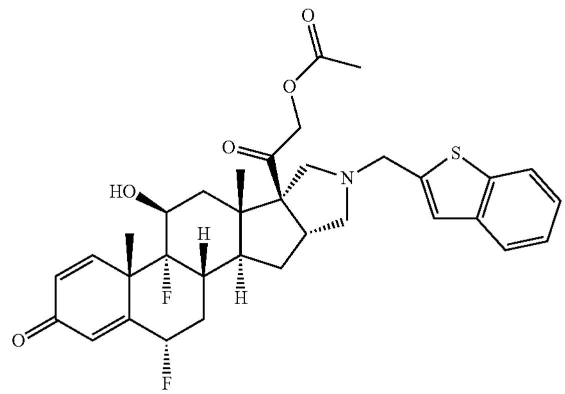 | 51% | LC-MS (ESI POS): 610.3 MH+ |
| 14 | 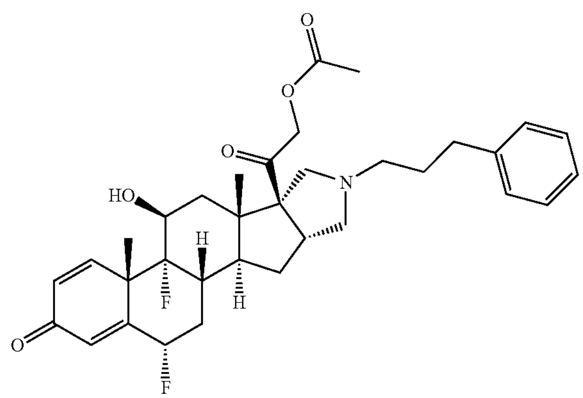 | 76% | LC-MS (ESI POS): 582.0 MH+ |

Compound 15 in Table 4 was prepared from compound 13 as described in Example 5 for the preparation of compound 9.

TABLE 4

| Compound | Structure | Yield | Analytical |
|---|---|---|---|
| 15 | 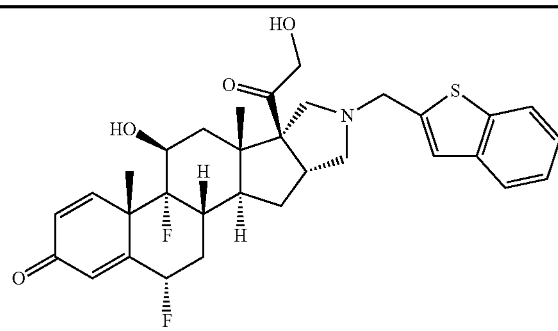 | 64% | ¹H NMR (300 MHz, DMSO-d₆) δ ppm 7.82-7.94 (m, 1 H), 7.67-7.76 (m, 1 H), 7.23-7.41 (m, 3 H), 7.22 (s, 1 H), 6.29 (dd, 1 H), 6.14 (s, 1 H), 5.49-5.81 (m, 1 H), 5.40 (d, 1 H), 4.84 (t, 1 H), 4.28 (dd, 1 H), 4.11-4.21 (m, 1 H), 4.14 (dd, 1 H), 3.79 (d, 1 H), 3.73 (d, 1 H), 3.10-3.25 (m, 1 H), 2.96 (t, 1 H), 2.62 (d, 1 H), 2.55-2.60 (m, 2 H), 1.95-2.34 (m, 3 H), 1.79-1.90 (m, 1 H), 1.53-1.79 (m, 3 H), 1.49 (s, 3 H), 1.38 (dd, 1 H), 0.87 (s, 3 H) LC-MS (ESI POS): 568.28 MH+ $[\alpha]_D^{25}$ + 94.9 (c 0.35, MeOH) |

Example 7

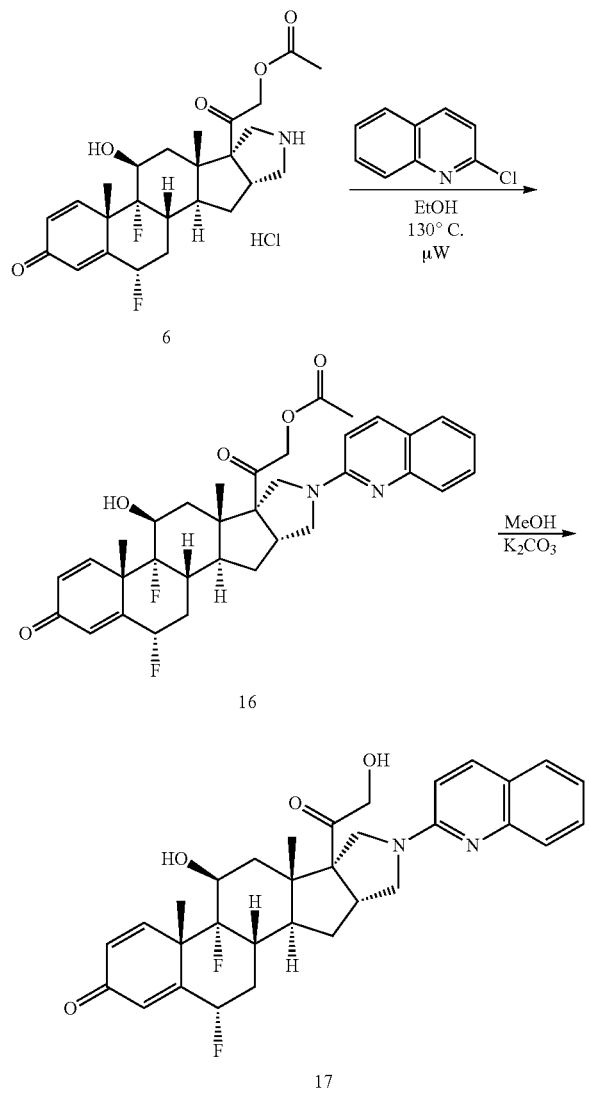

Preparation of Acetic acid 2-((4aS,4bR,5S,6aS,6bS, 9aR,10aS,10bS,12S)-4b,12-difluoro-5-hydroxy-4a, 6a-dimethyl-2-oxo-8-quinolin-2-yl-2,4b,5,6,6a,7,8,9, 9a,10,10a,10b,11,12-tetradecahydro-4aH-8-aza-pentaleno[2,1-a]phenanthren-6b-yl)-2-oxo-ethyl ester (compound 16)

Intermediate 6 (200 mg, 0.400 mmol) and 2-chloroquinoline (131 mg, 0.800 mmol) were placed in microwave vessel with EtOH (5 ml), and the reaction mixture was heated to 130° C. for 2 hours by microwaves. The mixture was partitioned between AcOEt and NaHCO$_3$ (5% solution). The organic phase was separated, dried over Na$_2$SO$_4$ and evaporated to give a residue that was purified by a silica gel cartridge (DCM/MeOH 99:1 to 95:5) to give the title compound (171 mg, 72% yield).

LC-MS (ESI POS): 591.3 (MH+)

Preparation of (4aS,4bR,5S,6aS,6bS,9aR,10aS,10bS, 12S)-4b,12-Difluoro-5-hydroxy-6b-(2-hydroxy-acetyl)-4a,6a-dimethyl-8-quinolin-2-yl-4b,5,6,6a,6b, 7,8,9,9a,10,10a,10b,11,12-tetradecahydro-4aH-8-aza-pentaleno[2,1-a]phenanthren-2-one (compound 17)

A solution of compound 16 (171 mg, 0.290 mmol) in MeOH (4 ml) was degassed bubbling nitrogen at RT for 20 minutes. After cooling to 0° C. K$_2$CO$_3$ (12 mg, 0.0.87 mmol) was added, and the mixture was stirred for 1 hour. The mixture was partitioned between AcOEt and brine. The organic phase was separated, dried over Na$_2$SO$_4$ and concentrated. The crude was purified by preparative HPLC(CH$_3$CN/H$_2$O without CF$_3$COOH) to give the title compound (45 mg, 28% yield).

$^1$H NMR (300 MHz, DMSO-d$_6$) δ ppm 8.00 (d, 1H), 7.68 (d, 1H), 7.43-7.60 (m, 2H), 7.27 (dd, 1H), 7.19 (ddd, 1H), 6.94 (d, 1H), 6.29 (dd, 1H), 6.07 (s, 1H), 5.52-5.81 (m, 1H), 5.49 (dd, 1H), 4.94 (t, 1H), 4.50 (dd, 1H), 4.20-4.28 (m, 1H), 4.16 (dd, 1H), 3.78 (dd, 1H), 3.72 (d, 1H), 3.57 (d, 1H), 3.34-3.54 (m, 2H), 2.54-2.70 (m, 2H), 2.12-2.31 (m, 1H), 1.76-2.10 (m, 4H), 1.52-1.66 (m, 1H), 1.50 (s, 3H), 1.03 (s, 3H)

LC-MS (ESI POS): 549.32 (MH+)

[α]$_D^{25}$+37.3 (c 0.45, MeOH)

Compound 18 in Table 5 was prepared by a two steps procedure as described in Example 7 for compound 17, starting from intermediate 6 and 2-chloro-1H-benzo[d]imidazole.

| Compound | Structure | Yield | Analytical |
|---|---|---|---|
| 18 | 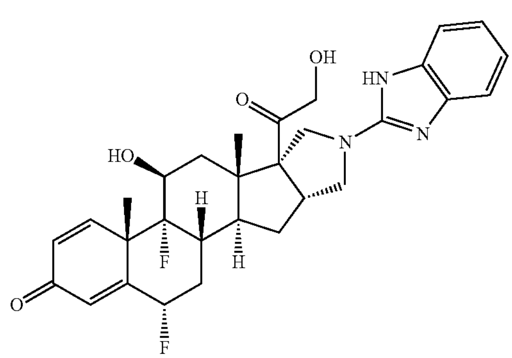 | 32% | $^1$H NMR (300 MHz, DMSO-d$_6$) δ ppm 7.40-7.57 (m, 2 H), 7.25 (dd, 1 H), 6.82-7.00 (m, 2 H), 6.28 (dd, 1 H), 6.04-6.13 (m, 1 H), 5.54-5.75 (m, 1 H), 5.51 (dd, 1 H), 4.95 (t, 1 H), 4.47 (dd, 1 H), 4.27 (dd, 1 H), 4.17-4.23 (m, 1 H), 4.14 (t, 1 H), 3.51-3.70 (m, 1 H), 2.56-2.73 (m, 2 H), 1.96-2.24 (m, 2 H), 1.63-1.85 (m, 3 H), 1.52-1.63 (m, 2 H), 1.49 (s, 3 H), 0.90 (s, 3 H) LC-MS (ESI POS): 578.16 (MH+) [α]$_D^{25}$ + 10.1 (c 0.57, MeOH) |

Example 8

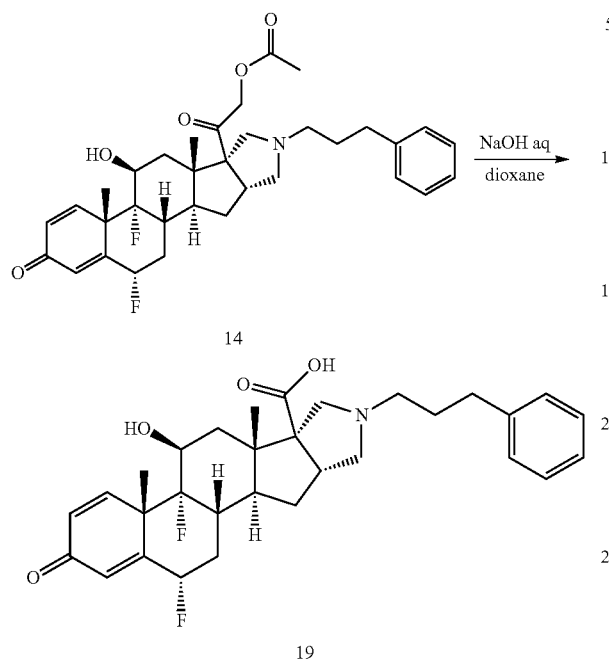

Preparation of Acetic acid 2-[(4aS,4bR,5S,6aS,6bS, 9aR,10aS,10bS,12S)-8-(1H-benzoimidazol-2-yl)-4b, 12-difluoro-5-hydroxy-4a,6a-dimethyl-2-oxo-2,4b,5, 6,6a,7,8,9,9a,10,10a,10b,11,12-tetradecahydro-4aH-8-aza-pentaleno[2,1-a]phenanthren-6b-yl]-2-oxo-ethyl ester (intermediate 19)

A solution of compound 14 (800 mg, 1.375 mmol) and 6 N aqueous NaOH (1031 μl, 6.19 mmol) in dioxane (45 ml) and water (15 ml) was stirred at RT in open air for 18 hours. HCl 6N (1 ml) was added to the reaction mixture until the pH was 4-5, then the organic solvent was evaporated and a solid precipitated, which was recovered by filtration. Mother liquors were extracted with AcOEt, and the combined organics were washed with brine, dried over Na$_2$SO$_4$ and concentrated to dryness affording a solid that was combined to the previously obtained one. The solid was triturated with Et$_2$O, to give the title intermediate (667 mg, 92% yield).

LC-MS (ESI POS): 526.0 MH+

Example 9

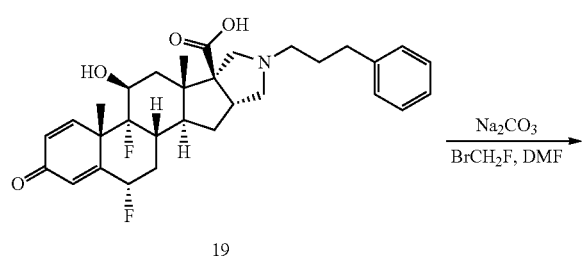

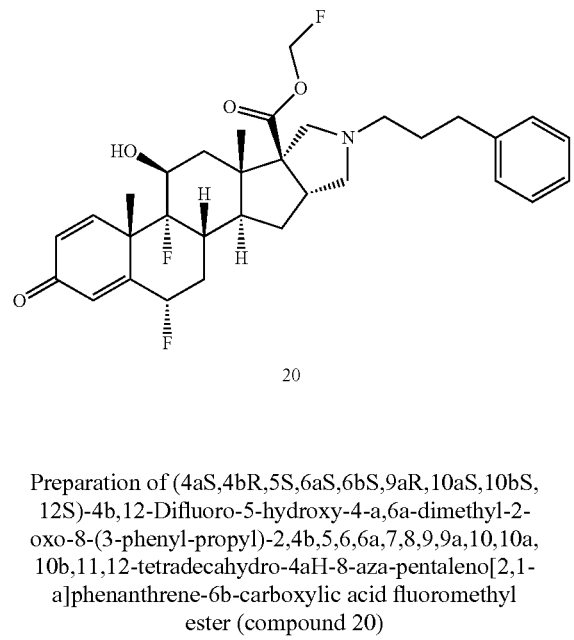

Preparation of (4aS,4bR,5S,6aS,6bS,9aR,10aS,10bS, 12S)-4b,12-Difluoro-5-hydroxy-4-a,6a-dimethyl-2-oxo-8-(3-phenyl-propyl)-2,4b,5,6,6a,7,8,9,9a,10,10a, 10b,11,12-tetradecahydro-4aH-8-aza-pentaleno[2,1-a]phenanthrene-6b-carboxylic acid fluoromethyl ester (compound 20)

To a solution of intermediate 19 (150 mg, 0.285 mmol) in dry DMF (4 ml), Na$_2$CO$_3$ (60.5 mg, 0.571 mmol) was added, and the suspension stirred at RT for 15 minutes, then the reaction was cooled to 0° C., and bromofluoromethane (285 μl, 0.571 mmol) was added. After stirring at 0° C. overnight, Na$_2$CO$_3$ (181 mg, 1.707 mmol) and bromofluoromethane (570 μl, 1.140 mmol) were added, and the mixture was stirred at RT overnight. The reaction was diluted with AcOEt and poured onto brine, the aqueous layer was extracted with AcOEt twice, and the combined organic extracts were washed with brine. After solvent removal, the crude was purified by silica gel chromatography (DCM/AcOEt 85:15) to give the title compound (60 mg, 38% yield).

$^1$H NMR (300 MHz, DMSO-d$_6$) δ ppm 7.26 (dd, 1H), 7.06-7.27 (m, 5H), 6.29 (dd, 1H), 6.10 (s, 1H), 5.80 (dd, 1H), 5.79 (dd, 3H), 5.51-5.73 (m, 1H), 5.50 (dd, 1H), 4.06-4.28 (m, 1H), 2.99-3.18 (m, 1H), 2.84 (t, 1H), 2.63 (d, 1H), 2.54 (d, 1H), 2.40-2.58 (m, 3H), 2.13-2.34 (m, 2H), 2.06 (dd, 1H), 1.95-2.03 (m, 1H), 1.53-1.91 (m, 5H), 1.49 (s, 3H), 1.36 (dd, 1H), 0.98 (s, 3H))

LC-MS (ESI POS): 558.28 MH+

[α]$_D^{20}$ +56.52 (c 0.27, MeOH)

Example 10

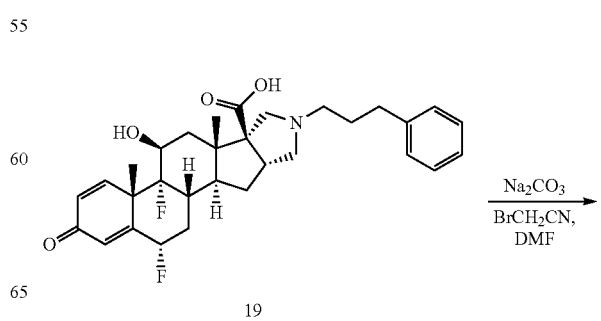

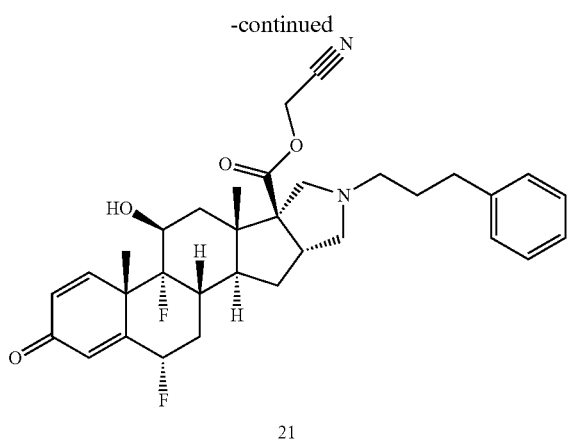

21

Preparation of (4aS,4bR,5S,6aS,6bS,9aR,10aS,10bS, 12S)-4b,12-Difluoro-5-hydroxy-4-a,6a-dimethyl-8- (5-methyl-furan-2-ylmethyl)-2-oxo-2,4b,5,6,6a,7,8, 9,9a,10,10a,10b,11,12-tetradecahydro-4aH-8-aza- pentaleno[2,1-a]phenanthrene-6b-carboxylic acid cyanomethyl ester (compound 21)

To a solution of intermediate 19 (151 mg, 0.287 mmol) in dry DMF (4 ml), Na$_2$CO$_3$ (54.8 mg, 0.517 mmol) was added, and the suspension stirred at RT for 20 minutes. After cooling to 0° C. 2-bromoacetonitrile (0.018 ml, 0.259 mmol) was added, and the mixture was stirred for 3 hours. Then, Na$_2$CO$_3$ (24 mg, 0.230 mmol) and 2-bromoacetonitrile (8.00 μl, 0.114 mmol) were added, and the mixture was stirred 48 hours. The reaction was diluted with AcOEt and poured onto brine, the aqueous layer was extracted with AcOEt twice, and the combined organic extracts were washed with brine. After solvent removal, the crude was purified by silica gel chromatography (DCM/AcOEt 3:1 to 1:1) to title compound (75 mg, 46% yield).

$^1$H NMR (300 MHz, DMSO-d6) δ ppm 7.05-7.34 (m, 6H), 6.29 (dd, 1H), 6.10 (s, 1H), 5.54-5.76 (m, 1H), 5.53 (dd, 1H), 5.02 (s, 2H), 4.03-4.28 (m, 1H), 3.01-3.17 (m, 1H), 2.83 (t, 1H), 2.55-2.68 (m, 4H), 2.40-2.47 (m, 2H), 2.14-2.35 (m, 3H), 1.92-2.12 (m, 2H), 1.50 (s, 3H), 1.43-1.88 (m, 5H), 1.29-1.42 (m, 1H), 0.97 (s, 3H)

LC-MS (ESI POS): 565.29 MH+

[α]$_D^{25}$+71.3 (c 0.29, MeOH)

Example 11

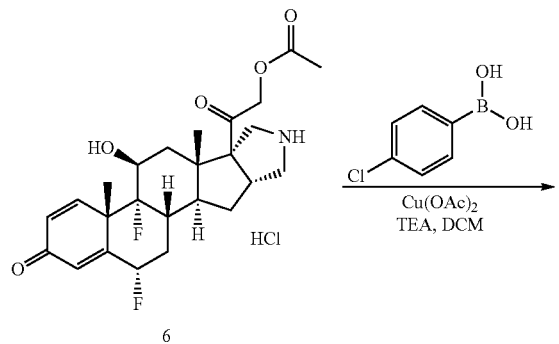

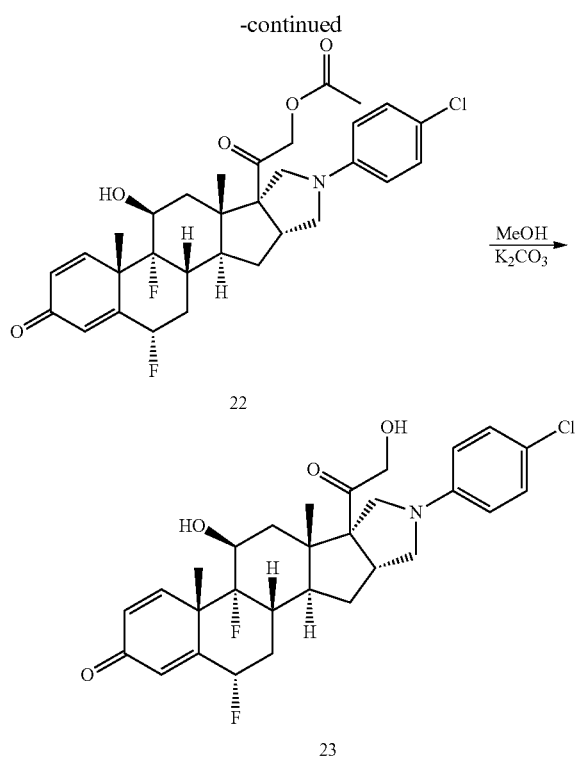

Preparation of Acetic acid 2-[(4aS,4bR,5S,6aS,6bS, 9aR,10aS,10bS,12S)-8-(4-chloro-phenyl)-4b,12- difluoro-5-hydroxy-4a,6a-dimethyl-2-oxo-2,4b,5,6, 6a,7,8,9,9a,10,10a,10b,11,12-tetradecahydro-4aH-8- aza-pentaleno[2,1-a]phenanthren-6b-yl]-2-oxo-ethyl ester (compound 22)

Intermediate 6 (250 mg, 0.500 mmol) and 4-chlorophenyl-boronic acid (235 mg, 1.500 mmol) were dissolved in DCM (10 ml), then triethylamine (0.485 ml, 3.50 mmol), and copper(II) acetate (91 mg, 0.500 mmol) were added, and the reaction mixture was stirred at RT for 15 days. The resulting suspension was filtered off, and the solvent was evaporated. The crude was purified by silica gel flash chromatography (eluent DCM/MeOH 99:1 to 98:2) to yield the title compound (35 mg, 12%).

$^1$H NMR (300 MHz, DMSO-d6) δ ppm 7.27 (d, 1H), 7.03-7.23 (m, 2H), 6.48-6.77 (m, 2H), 6.29 (dd, 1H), 6.09 (s, 1H), 5.50-5.77 (m, 1H), 5.47 (dd, 1H), 5.12 (d, 1H), 4.78 (d, 1H), 4.04-4.27 (m, 1H), 3.30-3.55 (m, 4H), 3.11 (dd, 1H), 2.57-2.69 (m, 1H), 2.14-2.34 (m, 1H), 2.08 (s, 3H), 1.69-2.02 (m, 4H), 1.51-1.63 (m, 1H), 1.50 (s, 3H), 1.37-1.49 (m, 1H), 1.05 (s, 3H)

LC-MS (ESI POS): 574.3 MH+

Preparation of (4aS,4bR,5S,6aS,6bS,9aR,10aS,10bS, 12S)-8-(4-Chloro-phenyl)-4b,12-difluoro-5-hydroxy- 6b-(2-hydroxy-acetyl)-4a,6a-dimethyl-4b,5,6,6a,6b, 7,8,9,9a,10,10a,10b,11,12-tetradecahydro-4aH-8- aza-pentaleno[2,1-a]phenanthren-2-one (compound 23)

Compound 22 (33 mg, 0.057 mmol) was hydrolyzed as described in Example 5 for the synthesis of compound 9. Title compound 23 (24 mg, 78%) was isolated by silica gel flash chromatography (eluent DCM/MeOH 99:1 to 98:2).

¹H NMR (300 MHz, DMSO-d₆) δ ppm 7.26 (dd, 1H), 7.10-7.22 (m, 2H), 6.52-6.72 (m, 2H), 6.29 (dd, 1H), 6.09 (s, 1H), 5.49-5.74 (m, 1H), 5.45 (dd, 1H), 4.92 (t, 1H), 4.45 (dd, 1H), 4.13-4.27 (m, 1H), 4.12 (dd, 1H), 3.43-3.55 (m, 1H), 3.34-3.43 (m, 3H), 3.06 (dd, 1H), 2.59-2.67 (m, 1H), 2.18-2.34 (m, 1H), 1.71-2.00 (m, 4H), 1.52-1.59 (m, 1H), 1.50 (s, 3H), 1.37-1.48 (m, 1H), 0.99 (s, 3H)

LC-MS (ESI POS): 532.28 MH+

[α]$_D^{25}$ +19.3 (c 0.26, MeOH)

Compound 24 reported in Table 6 was prepared by a two step procedure as described in Example 11 for compound 23, starting from intermediate 6 and 3-chlorophenylboronic acid.

| Compound | Structure | Yield | Analytical |
|---|---|---|---|
| 24 | 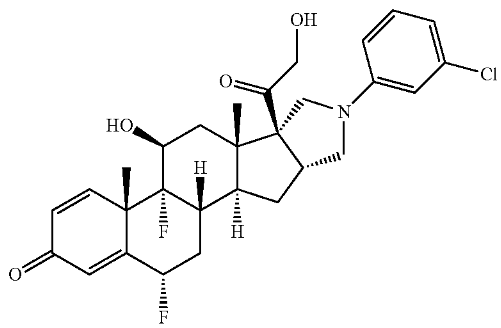 | 10% | ¹H NMR (300 MHz, DMSO-d₆) δ ppm 7.26 (dd, 1 H), 7.14 (t, 1 H), 6.62-6.74 (m, 2 H), 6.53-6.61 (m, 1 H), 6.29 (dd, 1 H), 6.09 (s, 1 H), 5.49-5.75 (m, 1 H), 5.45 (br. s., 1 H), 4.92 (br. s., 1 H), 4.47 (d, 1 H), 4.17-4.27 (m, 1 H), 4.12 (d, 1 H), 3.48 (d, 1 H), 3.33-3.43 (m, 3 H), 3.11 (dd, 1 H), 2.54-2.68 (m, 1 H), 2.14-2.35 (m, 1 H), 1.67-2.03 (m, 4 H), 1.53-1.60 (m, 1 H), 1.50 (s, 3 H), 1.34-1.48 (m, 1 H), 0.99 (s, 3 H) LC-MS (ESI POS): 532.33 MH+ [α]$_D^{25}$ + 18.1 (c 0.4, MeOH) |

Example 12

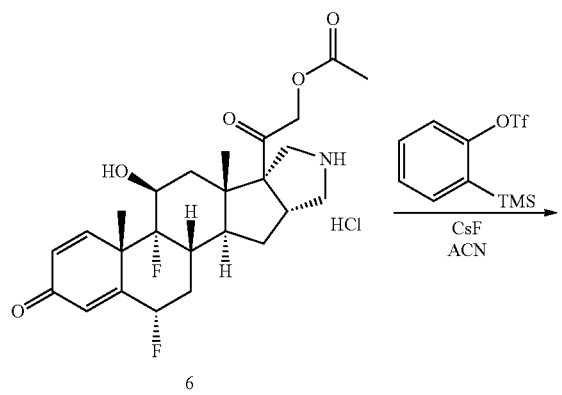

Preparation of Acetic acid 2-((4aS,4bR,5S,6aS,6bS, 9aR,10aS,10bS,12S)-4b,12-difluoro-5-hydroxy-4a, 6a-dimethyl-2-oxo-8-phenyl-2,4b,5,6,6a,7,8,9,9a,10, 10a,10b,11,12-tetradecahydro-4aH-8-aza-pentaleno [2,1-a]phenanthren-6b-yl)-2-oxo-ethyl ester (intermediate 25)

In a nitrogen atmosphere compound 6 (150 mg, 0.300 mmol) was suspended in acetonitrile (4 ml). 2-(trimethylsilyl)phenyl trifluoromethanesulfonate (0.146 ml, 0.600 mmol) and CsF (182 mg, 1.200 mmol) were added, and the mixture was stirred for 45 minutes at RT. Additional CsF (137 mg, 0.900 mmol) (not dried) was added, and the mixture was stirred for 5 hours, and then it is was poured in water. Acetonitrile was evaporated, and the reaction mixture was partitioned between water and AcOEt. The organic layer was separated dried over Na₂SO₄ and concentrated. The crude was purified by silica gel flash chromatography (eluent DCM/MeOH 98:2) affording the title intermediate (49 mg, 30.3% yield).

LC-MS (ESI POS): 540.2 (MH+)

Example 13

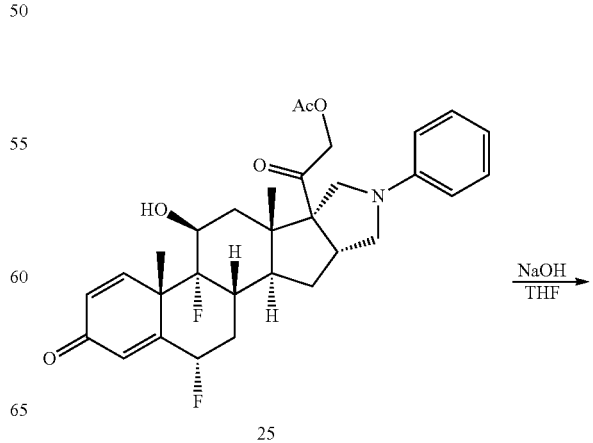

2.02-2.14 (m, 1H), 1.74-2.02 (m, 3H), 1.52-1.63 (m, 1H), 1.50 (s, 3H), 1.37-1.48 (m, 1H), 1.08 (s, 3H)
LC-MS (ESI POS): 532.30 MH+
$[\alpha]_D^{25}$ +12.4 (c 0.34, MeOH)

Example 14

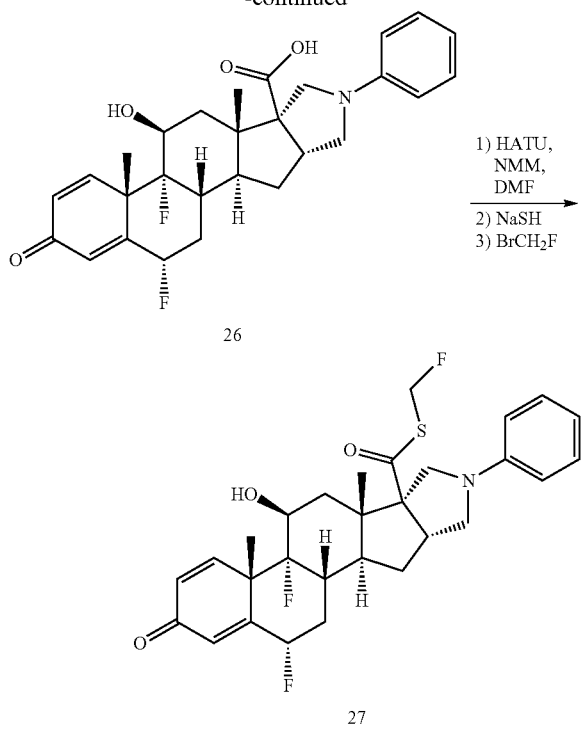

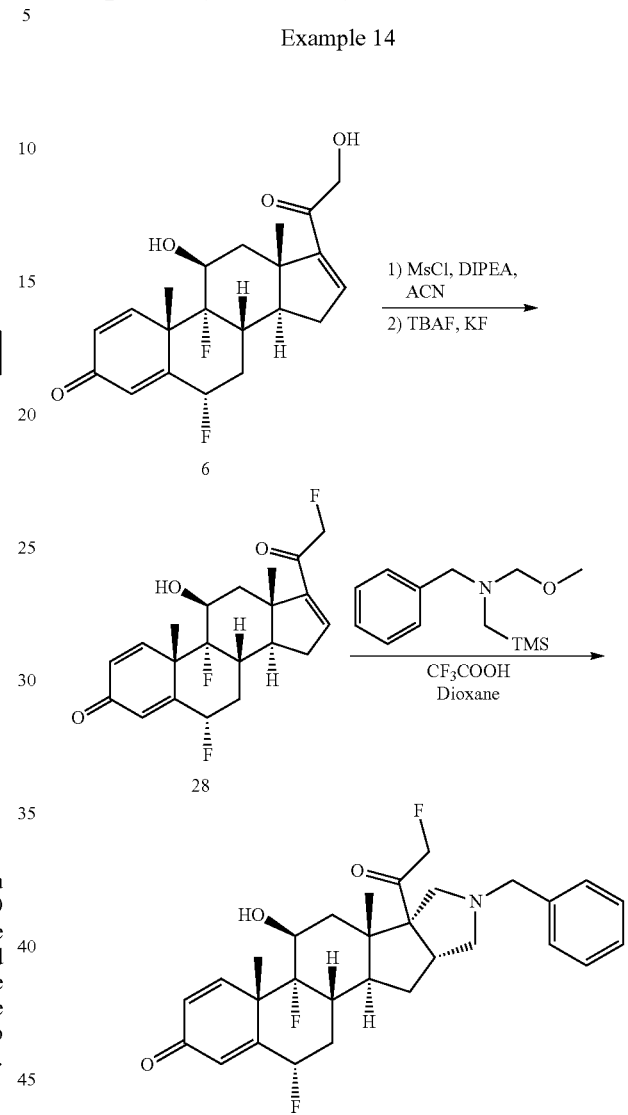

Preparation of (4aS,4bR,5S,6aS,6bS,9aR,10aS,10bS,12S)-4b,12-Difluoro-5-hydroxy-4-a,6a-dimethyl-2-oxo-8-phenyl-2,4b,5,6,6a,7,8,9,9a,10,10a,10b,11,12-tetradecahydro-4-aH-8-aza-pentaleno[2,1-a]phenanthrene-6b-carboxylic acid (compound 26)

Intermediate 25 (550 mg, 1.019 mmol) was dissolved in a THF/water 2/1 mixture (15 ml), 2M aqueous NaOH (2.039 ml, 4.08 mmol) was added, and the mixture was stirred in the open air for 1.5 hours. The reaction mixture was neutralized by adding 3N HCl solution. THF was evaporated, and the mixture was partitioned between AcOEt and water. The organic phase was dried over $Na_2SO_4$ and concentrated to dryness affording the title compound (493 mg, quant. yield).
LC-MS (ESI POS): 484.3 MH+

(4aS,4bR,5S,6aS,6bS,9aR,10aS,10bS,12S)-4b,12-Difluoro-5-hydroxy-4a,6a-dimethyl-2-oxo-8-phenyl-2,4b,5,6,6a,7,8,9,9a,10,10a,10b,11,12-tetradecahydro-4aH-8-aza-pentaleno[2,1-a]phenanthrene-6b-carbothioic acid S-fluoromethyl ester (compound 27)

A mixture of compound 26 (493 mg, 1.019 mmol), HATU (387 mg, 1.1019 mmol) and N-methylmorpholine (0.123 ml, 1.121 mmol) in dry DMF (7 ml) was stirred at RT under nitrogen for 40 minutes. Then, anhydrous sodium hydrogen sulfide (171 mg, 3.06 mmol) was added, and the solution was stirred at RT for 1 hour. Bromofluoromethane (2.038 ml, 4.08 mmol, 2 M solution in DMF) was added, and the mixture was stirred at RT for 2 hours. The reaction mixture was concentrated to dryness and the crude was purified by preparative HPLC($CH_3CN/H_2O$, without $CF_3COOH$) to afford the title compound (158 mg, 29% yield).
$^1H$ NMR (300 MHz, DMSO-$d_6$) δ ppm 7.26 (dd, 1H), 7.04-7.21 (m, 2H), 6.60-6.79 (m, 3H), 6.30 (dd, 1H), 6.09 (s, 1H), 5.95 (dd, 1H), 5.91 (dd, 1H), 5.58 (dd, 1H), 5.47-5.76 (m, 1H), 4.04-4.36 (m, 1H), 3.61 (dd, 1H), 3.48 (d, 1H), 3.34 (d, 1H), 3.05 (dd, 1H), 2.56-2.70 (m, 2H), 2.14-2.32 (m, 1H),

Preparation of (6S,8S,9R,10S,11S,13S,14S)-6,9-difluoro-17-(2-fluoroacetyl)-11-hydroxy-10,13-dimethyl-6,7,8,9,10,11,12,13,14,15-decahydro-3H-cyclopenta[a]phenanthren-3-one (intermediate 28)

In a nitrogen atmosphere, intermediate 3 (100 mg, 0.264 mmol) was dissolved in acetonitrile (4 ml), and Mesyl-Cl (32 µl, 0.411 mmol) and DIPEA (78 µl, 0.447 mmol) were added. The mixture was stirred at RT for 30 minutes. Potassium fluoride (154 mg, 2.64 mmol) was added, and the mixture was stirred for 1 h at 60° C. TBAF 1M in THF (529 µl, 0.529 mmol) was added, and the mixture is stirred at 60° C. for 4 hours. The reaction mixture was partitioned between water and AcOEt, the organic layer was separated, dried over $Na_2SO_4$ and concentrated. The crude was purified by silica gel flash chromatography (eluent DCM/AcOEt=1:1) to yield intermediate 28 (62 mg, 61.7% yield).
LC-MS (ESI POS): 381.0 (MH+)

Preparation of (4aS,4bR,5S,6aS,6bS,9aR,10aS,10bS, 12S)-8-Benzyl-4b,12-difluoro-6b-(2-fluoro-acetyl)-5-hydroxy-4a,6a-dimethyl-4b,5,6,6a,6b,7,8,9,9a,10, 10a,10b,11,12-tetradecahydro-4aH-8-aza-pentaleno[2,1-a]phenanthren-2-one (intermediate 29)

In a closed vessel, to a mixture of intermediate 28 (125 mg, 0.329 mmol) and N-benzyl-1-methoxy-N-((trimethylsilyl)methyl)methanamine (0.318 ml, 1.314 mmol) in 1,4-dioxane (5 ml), 1 drop of TFA (cat) was added, and the mixture was stirred at 100° C. for 1 hour. The reaction mixture was concentrated and purified by silica gel flash chromatography (eluent DCM/AcOEt 7:3) and then by preparative HPLC to afford the title intermediate (45 mg, 26.7% yield).

$^1$H NMR (300 MHz, DMSO-$d_6$) δ ppm 7.11-7.47 (m, 6H), 6.29 (dd, 1H), 6.12 (s, 1H), 5.49-5.77 (m, 1H), 5.40 (dd, 1H), 5.26 (dd, 1H), 5.11 (dd, 1H), 4.05-4.22 (m, 1H), 3.49 (d, 1H), 3.44 (d, 1H), 3.03-3.19 (m, 1H), 2.92 (t, 1H), 2.53-2.61 (m, 2H), 2.38 (d, 1H), 2.20-2.33 (m, 1H), 1.93-2.10 (m, 2H), 1.84 (d, 1H), 1.51-1.77 (m, 3H), 1.49 (s, 3H), 1.37 (dd, 1H), 0.91 (s, 3H)

LC-MS (ESI POS): 514.39 MH+
$[α]_D^{25}$ +84.2 (c 0.36 CHCl3)

Example 15

Preparation of (4aS,4bR,5S,6aS,6bS,9aR,10aS,10bS, 12S)-4b,12-Difluoro-6b-(2-fluoro-acetyl)-5-hydroxy-4a,6a-dimethyl-2-oxo-2,4b,5,6,6a,6b,7,9,9a, 10,10a,10b,11,12-tetradecahydro-4aH-8-aza-pentaleno[2,1-a]phenanthrene-8-carboxylic acid vinyl ester (intermediate 30)

Intermediate 29 (614 mg, 1.196 mmol) and NaHCO$_3$ (100 mg, 1.196 mmol) were dissolved in acetonitrile (12 ml), and then vinyl chloroformate (0.204 ml, 2.391 mmol) was added. The reaction mixture was warmed at 50° C. for 1 hour. The solution was partitioned between AcOEt and water. The organic phase was separated, and the aqueous solution was extracted with AcOEt. The combined organic phases were dried over Na$_2$SO$_4$ and then evaporated to give a residue that was purified by silica gel column chromatography (eluent AcOEt/petroleum ether 2:8 to 8:2) leading to the pure title intermediate (411 mg, 69.7% yield).

LC-MS (ESI POS): 494.0 MH+

Preparation of (4aS,4bR,5S,6aS,6bS,9aR,10aS,10bS, 12S)-4b,12-Difluoro-6b-(2-fluoro-acetyl)-5-hydroxy-4a,6a-dimethyl-4b,5,6,6a,6b,7,8,9,9a,10,10a, 10b,11,12-tetradecahydro-4aH-8-aza-pentaleno[2,1-a]phenanthren-2-one hydrochloride (intermediate 31)

Intermediate 30 (294 mg, 0.596 mmol) was dissolved in DCM (20 ml), and then HCl 4.0 M in dioxane (2.98 ml, 11.91 mmol) was added. The solution was stirred at RT for 5 hours, and then the solvent was evaporated, and the residue was dried under vacuum for 16 hours. The solid was then dissolved in methanol (30 ml) and warmed at 45° C. for 20 minutes. Methanol was evaporated to give the title intermediate (274 mg, 100% yield).

LC-MS (ESI POS): 424.0 (MH+)

Example 16

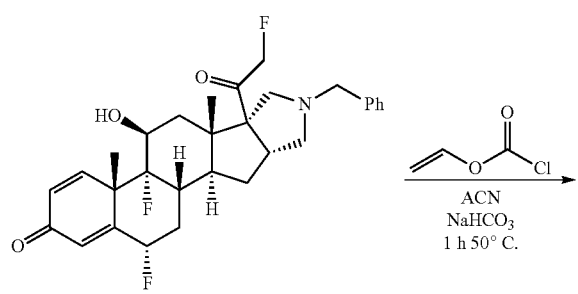

29

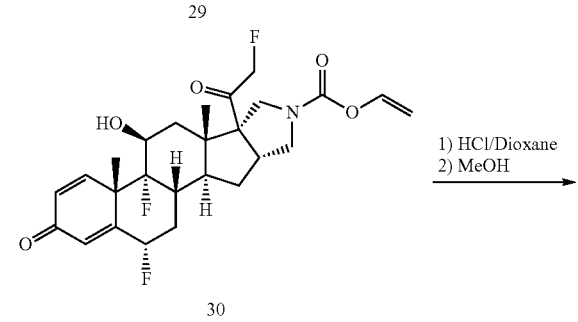

30

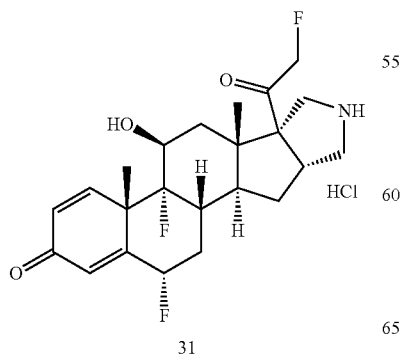

31

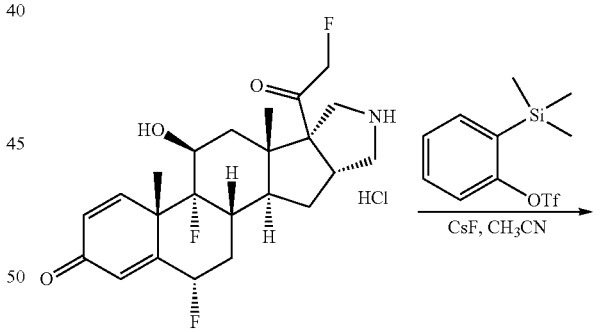

31

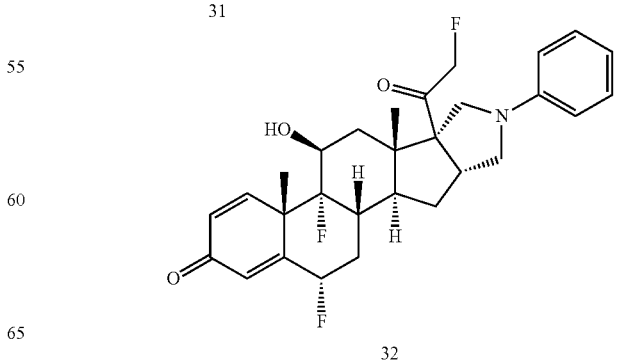

32

Preparation of (4aS,4bR,5S,6aS,6bS,9aR,10aS,10bS, 12S)-4b,12-Difluoro-6b-(2-fluoro-acetyl)-5-hydroxy-4a,6a-dimethyl-8-phenyl-4b,5,6,6a,6b,7,8,9, 9a,10,10a,10b,11,12-tetradecahydro-4aH-8-azapentaleno[2,1-a]phenanthren-2-one (compound 32)

Intermediate 31 (307 mg, 0.667 mmol) was suspended in acetonitrile (12 ml). CsF (406 mg, 2.67 mmol), 2-(trimethylsilyl)phenyl trifluoromethanesulfonate (239 mg, 0.194 mmol), and water (1 drop) were added, and the mixture was stirred at RT for 24 hours. The reaction mixture was partitioned between water and AcOEt, and the organic layer was separated, dried, and concentrated. The crude was purified by silica gel flash chromatography (eluent DCM/MeOH=99:1) to yield the title compound (94 mg, 28%).

$^1$H NMR (300 MHz, DMSO-$d_6$) δ ppm 7.27 (dd, 1H), 7.05-7.22 (m, 2H), 6.55-6.81 (m, 3H), 6.29 (dd, 1H), 6.08 (s, 1H), 5.50-5.74 (m, 1H), 5.46 (dd, 0H), 5.46 (dd, 1H), 5.14 (dd, 1H), 4.08-4.29 (m, 1H), 3.44-3.60 (m, 1H), 3.32-3.41 (m, 3H), 3.25 (d, 1H), 3.05 (dd, 1H), 2.55-2.69 (m, 1H), 2.15-2.34 (m, 1H), 1.70-2.00 (m, 4H), 1.51-1.59 (m, 1H), 1.50 (s, 3H), 1.39-1.48 (m, 1H), 1.03 (s, 3H)

Legend:
LC-MS (ESI POS): 500.31 MH+
$[\alpha]_D^{25}$ +24.1 (c=0.48, MeOH)
s=singlet
d=doublet
t=triplet
q=quartet
dd=doublet of doublets
m=multiplet
br=broad Pharmacological Activity of the Compounds of the Invention In Vitro Studies.

Example 17

Glucocorticoid Receptor (GR) Translocation Assay Protocol

A quantitative measurement of GR nuclear translocation of the compounds of the present invention was performed according to ASSAY Drug Devel. Technol., 4(3), 263-272, 2006, which is incorporated herein by reference in its entirety, through a novel cell-based GR-translocation assay in Enzyme Fragment Complementation (EFC) format developed by DiscoveRx (Fremont, Calif.).

The DiscoveRx assay uses EFC of b-galactosidase (b-gal) as an indicator of GR-translocation in engineered CHO—K1 biosensor cells. The enzyme acceptor (EA) fragment of b-gal resides in the nucleus, as designed through the use of a proprietary set of sequence additions and modifications. The small peptide enzyme donor (ED) fragment of b-gal is fused directly to the C-terminus of GR, and is localized in the cytoplasm is the absence of receptor signaling. Upon binding to a GR ligand, the complex translocates to the nucleus, where intact enzyme activity is restored by complementation and b-gal activity is detected.

CHO—K1 cells stably expressing NLS-enzyme acceptor fragment (EA) of b-gal and GR-enzyme donor (ED) fragment of b-gal were maintained in F12 medium (Invitrogen, Carlsbad, Calif.) at 37° C. under a humidified atmosphere containing 5% $CO_2$ and 95% air. The medium contained 10% FBS, 2 mM L-glutamine, 50 U/ml penicillin 50 µg/ml streptomycin, and 250 µg/ml hygromycin and 500 µg/ml G418 (Invitrogen).

GR-translocation was measured using the PathHunter Detection Kit containing cell membrane permeabilizing reagent and beta-gal substrate (DiscoveRx, Fremont, Calif.). All compounds were screened using varying concentrations ranging from $10^{-11}$ to $10^{-6}$ M. The assay was performed in 48-wells (105 cells/well). Incubation with screened compounds was performed at 37° C. for two hours. Detection was made by adding the detection buffer from the kit supplied by DiscoveRx and incubating at RT for one hour. Luminescence was detected by using a CENTRO LB 960 microplate reader (Berthold Technologies). Statistical analysis and determinations of EC50s were performed by using Prism-version 3.0 Graphpad Software (San Diego, Calif.).

The compounds assayed with the GR translocation assay displayed a EC50 comprised between 1 nM and 10 nM.

Example 18

Inhibition of LPS-Induced Nitric Oxide Production in RAW 264.7 Macrophages

An in vitro model based on macrophagic murine cell line RAW 264.7 was used for testing the anti-inflammatory effects of the corticosteroids of the present invention. During the inflammatory process, large amounts of nitric oxide (NO) are generated by the inducible isoforms of NO synthase (iNOS). Bacterial lipopolysaccharide (LPS) is commonly used in experimental settings to stimulate inflammatory responses in macrophages.

Cells were grown in a culture medium (RPMI supplemented with heat-inactivated 10% fetal calf serum, 2 mM glutamine, 100 U/ml penicillin, and 0.1 mg/ml streptomycin) without phenol red. Cell stimulation was elicited by incubating cells for 24 hours with LPS to final concentrations ranging from 100 ng/ml. Treatments with the compounds of the invention were carried out by adding such compounds vehicled in DMSO (0.1% final concentration) to the final desired concentrations 15 minutes before LPS exposure. As an index of nitric oxide production, the concentration of nitrite was measured in the conditioned media by using the Griess colorimetric reaction (J. Neuroimmunol., 150, 29-36, 2004, which is incorporated herein by reference in its entirety).

Statistical analysis and determinations of IC50s were performed by using Prism-version 3.0 Graphpad Software (San Diego, Calif.). The IC50 values tested on the compounds of the invention are comprised between 0.16 and 1 nM.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

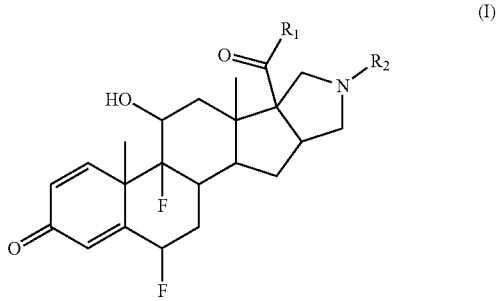

wherein:
$R_1$ is $(CH_2)_n$—V—$(CH_2)_{n'}$—$R_4$, wherein:

n and n' are independently 0 or 1;

V is absent or is —O—, —S—, or —OC(O)—; and $R_4$ is —H, —OH, —CN, halogen, or ($C_1$-$C_6$)alkyl, in which one or more of the hydrogen atoms of the alkyl group may be optionally substituted by one or more groups selected from the group consisting of oxo, —CN, —SH, and halogen;

$R_2$ is $(CH_2)_m$—$R_6$, wherein:

m=0 or an integer from 1 to 4; and $R_6$ is aryl or heteroaryl, each of which may be optionally substituted by one or more groups selected from the group consisting of oxo, —OH, —CN, —COOH, ($C_1$-$C_6$)alkoxy, ($C_1$-$C_6$)alkyl, ($C_1$-$C_6$)haloalkyl, and halogen;

or a pharmaceutically acceptable salt thereof.

2. A compound according to claim 1, which has formula (I'):

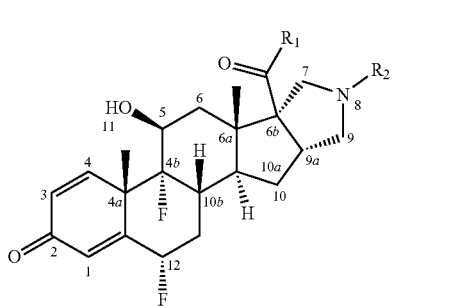

wherein the configuration of the carbon atom in position 4a is S, 4b is R, 5 is S, 6a is S, 6b is S, 9a is R, 10a is S, 10b is S, and 12 is S, or a pharmaceutically acceptable salt thereof.

3. A compound or salt thereof according to claim 1, wherein $R_1$ is $(CH_2)_n$—V—$(CH_2)_{n'}$—$R_4$, wherein n and n' are independently 0 or 1, V is absent or is —O—, —S—, or —OC(O) —, and $R_4$ is —H, —OH, —CN, halogen, or ($C_1$-$C_6$)alkyl in which one or more of the hydrogen atoms of the alkyl group may be optionally substituted by one or more groups selected from the group consisting of oxo, —CN, —SH, and halogen.

4. A compound or salt thereof according to claim 2, wherein $R_1$ is $(CH_2)_n$—V—$(CH_2)_{n'}$—$R_4$, wherein n and n' are independently 0 or 1, V is absent or is —O—, —S—, or —OC(O) —, and $R_4$ is —H, —OH, —CN, halogen, or ($C_1$-$C_6$)alkyl in which one or more of the hydrogen atoms of the alkyl group may be optionally substituted by one or more groups selected from the group consisting of oxo, —CN, —SH, and halogen.

5. A compound or salt thereof according to claim 3, wherein $R_1$ is $(CH_2)_n$—V—$(CH_2)_{n'}$—$R_4$, wherein n is 0 or 1 and n' is 0; V is —O— and $R_4$ is —H.

6. A compound or salt thereof according to claim 4, wherein $R_1$ is $(CH_2)_n$—V—$(CH_2)_{n'}$—$R_4$, wherein n is 0 or 1 and n' is 0; V is —O—, and $R_4$ is —H.

7. A compound or salt thereof according to claim 3, wherein $R_1$ is $(CH_2)_n$—V—$(CH_2)_{n'}$—$R_4$, wherein n is 0, V is —S— or —O—, n' is 1, and $R_4$ is fluorine or —CN.

8. A compound or salt thereof according to claim 4, wherein $R_1$ is $(CH_2)_n$—V—$(CH_2)_{n'}$—$R_4$, wherein n is 0, V is —S— or —O—, n' is 1, and $R_4$ is fluorine or —CN.

9. A compound or salt thereof according to claim 3, wherein $R_1$ is $(CH_2)_n$—V—$(CH_2)_{n'}$—$R_4$, wherein n is 1, V is absent, n' is 0, and $R_4$ is fluorine.

10. A compound or salt thereof according to claim 4, wherein $R_1$ is $(CH_2)_n$—V—$(CH_2)_{n'}$—$R_4$, wherein n is 1, V is absent, n' is 0, and $R_4$ is fluorine.

11. A compound or salt thereof according to claim 3, wherein $R_1$ is $(CH_2)_n$—V—$(CH_2)_{n'}$—$R_4$ wherein n is 1, V is —OC(O)—, n' is 1, and $R_4$ is —H.

12. A compound or salt thereof according to claim 4, wherein $R_1$ is $(CH_2)_n$—V—$(CH_2)_{n'}$—$R_4$ wherein n is 1, V is —OC(O)—, n' is 1, and $R_4$ is —H.

13. A compound or salt thereof according to claim 1, wherein $R_2$ is $(CH_2)_m$—$R_6$, wherein m=0 or an integer from 1 to 4; and $R_6$ is aryl or heteroaryl, each of which may be optionally substituted by one or more groups selected from the group consisting of oxo, —OH, —CN, —C(O)OH, ($C_1$-$C_6$)alkoxy, ($C_1$-$C_6$)alkyl, ($C_1$-$C_6$)haloalkyl, and halogen.

14. A compound or salt thereof according to claim 2, wherein $R_2$ is $(CH_2)_m$—$R_6$, wherein m=0 or an integer from 1 to 4; and $R_6$ is aryl or heteroaryl, each of which may be optionally substituted by one or more groups selected from the group consisting of oxo, —OH, —CN, —C(O)OH, ($C_1$-$C_6$)alkoxy, ($C_1$-$C_6$)alkyl, ($C_1$-$C_6$)haloalkyl, and halogen.

15. A compound or salt thereof according to claim 13, wherein $R_2$ is $(CH_2)_m$—$R_6$, wherein m=0, and $R_6$ is phenyl, benzoimidazolyl, or quinolinyl, each of which may be optionally substituted by one or more chlorine atoms.

16. A compound or salt thereof according to claim 14, wherein $R_2$ is $(CH_2)_m$—$R_6$, wherein m=0, and $R_6$ is phenyl, benzoimidazolyl, or quinolinyl, each of which may be optionally substituted by one or more chlorine atoms.

17. A compound or salt thereof according to claim 13, wherein $R_2$ is $(CH_2)_m$—$R_6$, wherein m=1, and $R_6$ is phenyl, quinolinyl, or benzothiophenyl, each of which may be optionally substituted by one or more chlorine atoms or methyl groups.

18. A compound or salt thereof according to claim 14, wherein $R_2$ is $(CH_2)_m$—$R_6$, wherein m=1, and $R_6$ is phenyl, quinolinyl, or benzothiophenyl, each of which may be optionally substituted by one or more chlorine atoms or methyl groups.

19. A compound or salt thereof according to claim 13, wherein $R_2$ is $(CH_2)_m$—$R_6$, wherein m=3 and $R_6$ is phenyl.

20. A compound or salt thereof according to claim 14, wherein $R_2$ is $(CH_2)_m$—$R_6$, wherein m=3 and $R_6$ is phenyl.

21. A pharmaceutical composition, comprising a compound or salt thereof according to claim 1 and one or more pharmaceutically acceptable carriers and/or excipients.

22. A combination, comprising a compound or salt thereof according to claim 1 and one or more active ingredients selected from the group consisting of a β2-agonist, an antimuscarinic agent, a PDE4 inhibitor, a P38 MAP kinase inhibitor, and an IKK2 inhibitor.

23. A method for the treatment of asthma, comprising administering, to a subject in need thereof, an effective amount of a compound or salt thereof according to claim 1.

24. A method for the treatment of chronic obstructive pulmonary disease, comprising administering, to a subject in need thereof, an effective amount of a compound or salt thereof according to claim 1.

* * * * *